United States Patent
Xiao et al.

(10) Patent No.: US 11,913,884 B2
(45) Date of Patent: Feb. 27, 2024

(54) VISIBLE LIGHT-ACTIVATED DYES AND METHODS OF USE THEREOF

(71) Applicant: William Marsh Rice University, Houston, TX (US)

(72) Inventors: Han Xiao, Houston, TX (US); Juan Tang, Houston, TX (US)

(73) Assignee: William Marsh Rice University, Houston, TX (US)

( * ) Notice: Subject to any disclaimer, the term of this patent is extended or adjusted under 35 U.S.C. 154(b) by 299 days.

(21) Appl. No.: 16/798,992

(22) Filed: Feb. 24, 2020

(65) Prior Publication Data

US 2020/0271587 A1 Aug. 27, 2020

Related U.S. Application Data

(60) Provisional application No. 62/810,023, filed on Feb. 25, 2019.

(51) Int. Cl.

| | | |
|---|---|---|
| *G01N 21/64* | (2006.01) | |
| *C07D 265/34* | (2006.01) | |
| *C07D 209/32* | (2006.01) | |
| *C07D 401/04* | (2006.01) | |
| *B82Y 15/00* | (2011.01) | |
| *A61K 49/00* | (2006.01) | |

(52) U.S. Cl.
CPC ....... *G01N 21/6486* (2013.01); *C07D 209/32* (2013.01); *C07D 265/34* (2013.01); *C07D 401/04* (2013.01); *G01N 21/6428* (2013.01); *A61K 49/0028* (2013.01); *B82Y 15/00* (2013.01)

(58) Field of Classification Search
CPC combination set(s) only.
See application file for complete search history.

(56) References Cited

U.S. PATENT DOCUMENTS

2018/0045738 A1* 2/2018 Mohan .............. G01N 33/6893

OTHER PUBLICATIONS

Qu et al., Polym. Chem. 2014, 5, 3396-3403. (Year: 2014).*
Patsenker et al., J. Mol. Structure 655 (2003) 311-320 (Year: 2003).*
Bates et al., "Multicolor super-resolution imaging with photoswitchable fluorescent probes", *Science*, 317(5845):1749-1753, 2007.
Brieke et al., "Light-controlled tools", *Angew. Chem. Int. Ed.*, 51(34):8446-8476, 2012.
Choi et al., "Hg 2+-selective chromogenic and fluorogenic chemodosimeter based on thiocoumarins", *Chem. Commun.*, 24:3560-3562, 2009.
Chozinski et al., "Twinkle, twinkle little star: Photoswitchable fluorophores for super-resolution imaging", *FEBS Lett.*, 588(19):3603-3612, 2014.
Corsaro and Pistarà, "Conversion of the thiocarbonyl group into the carbonyl group", *Tetrahedron*, 54(50):15027-15062, 1998.
Coyle, "The photochemistry of thiocaonyl compounds", *Tetrahedron*, 41(23):5393-5425, 1985.
Davis et al., "Fluorogenic label for biomolecular imaging", *ACS Chem. Biol.*, 1(4):252-260, 2006.
Goldberg et al., "Minimalist probes for studying protein dynamics: thioamide quenching of selectively excitable fluorescent amino acids", *J. Am. Chem. Soc.*, 134(14):6088-6091, 2012.
Goldberg et al., "Thioamide quenching of fluorescent probes through photoinduced electron transfer: mechanistic studies and applications", *J. Am. Chem. Soc.*, 135(49):18651-18658, 2013.
Goldberg et al., "Thioamides as fluorescence quenching probes: minimalist chromophores to monitor protein dynamics", *J. Am. Chem. Soc.*, 132(42):14718-14720, 2010.
Grimm et al., "Bright photoactivatable fluorophores for single-molecule imaging", *Nat. Methods*, 13(12):985-988, 2016.
Grimm et al., In: Progress in Molecular Biology and Translational Science; Morris, M. C., Ed.; Fluorescence—Based Biosensors; Academic Press, 113:1-34, 2013.
Huang et al., "Electronic interactions of i, i+ 1 dithioamides: increased fluorescence quenching and evidence for n-to-π* interactions", *Chem. Commun.*, 52(50):7798-7801, 2016.
Lee et al., "Fluorogenic Label for Biomolecular Imaging ", *ACS Chem. Biol.*, 4(6):409-427, 2009.
Li and Zheng, "Photoactivatable fluorophores and techniques for biological imaging applications", *Photochem. Photobiol. Sci.*, 11(3):460, 2012.
Moon et al., "Dual signaling of hypochlorous acid by desulfurization of thiocoumarin", *Tetrahedron Lett.*, 53(48):6594-6597, 2012.
Park et al., "Colorimetric and Fluorescent Signaling of Au3+ by Desulfurization of Thiocoumarin", *Inorg. Chem.*, 51(5):2880-2884, 2012.
Puliti et al., "Small photoactivatable molecules for controlled fluorescence activation in living cells", *Bioorg. Med. Chem.*, 19(3):1023-1029, 2011.
Sengupta et al., "Superresolution imaging of biological systems using photoactivated localization microscopy", *Chem. Rev.*, 114(6):3189-3202, 2014.

* cited by examiner

*Primary Examiner* — Robert S Cabral
(74) *Attorney, Agent, or Firm* — Parker Highlander PLLC

(57) ABSTRACT

Disclosed herein are photoactivable fluorophores comprising one or more thiocarbonyl groups as well as conjugates and compositions thereof. The present disclosure also provides methods of preparing photoactivatable fluorophores as well as methods of imaging using the photoactivatable fluorophores, conjugates, and compositions of the present disclosure.

16 Claims, 15 Drawing Sheets
(14 of 15 Drawing Sheet(s) Filed in Color)

VISIBLE LIGHT-ACTIVATED DYES AND METHODS OF USE THEREOF

This application claims the benefit of priority to U.S. Provisional Application No. 62/810,023, filed on Feb. 25, 2019, the entire contents of which are hereby incorporated by reference.

BACKGROUND

I. Field

The present disclosure relates generally to the fields of chemistry, biology, and imaging. More particularly, it concerns photoactivatable fluorophores as well as conjugates and compositions thereof. The present disclosure also concerns methods for the preparation of photoactivatable fluorophores and methods of imaging therewith.

II. Description of Related Art

Photoactivatable fluorophores, also called photocaged fluorophores, are powerful tools for improving the temporal and spatial resolution of subcellular structures and dynamics and are emerging as an important class of optical probes for biological imaging (Lavis et al., 2006, Puliti et al., 2011, Li et al., 2012, Brieke et al., 2012, Grimm et al., 2013, Chozinski et al., 2014, Grimm et al., 2016). Upon irradiation with light of appropriate wavelengths, these photocaged fluorophores undergo photochemical reactions to release the caged groups, thus regenerating fluorophores in their active forms. Because of their ability to pin-point turn on the target of interest in complex biological systems, photoactivatable fluorophores afford powerful tools for high resolution tracking of biological processes in living cells, tissues, and animals. Recently, sequential imaging of photoactivatable fluorophore-labeled molecules has enabled super-resolution imaging beyond the diffraction limit (e.g., Photoactivated Localization Microscopy (PALM), Stochastic Optical Reconstruction Microscopy (STORM)), revealing previously unobserved details of subcellular structures and biological processes (Bates et al., 2007, Sengupta et al., 2014).

To develop photoactivatable probes for biological studies, photocleavable "cage" functional groups, including o-nitrobenzyl, phenacyl, azidophenyl, xanthenyl, and ohydroxynaphthyl moieties, have been conjugated to fluorophores (Lee et al., 2009, Puliti et al., 2011, Brieke et al., 2012, Li et al., 2012). In general, the resulting photoactivatable fluorophores have relatively large size and can only be efficiently cleaved by irradiation with ultraviolet light, dramatically limiting their application for biological studies. To avoid the use of UV irradiation, researchers have explored the use of indirectly visible and nearinfrared light absorbing approaches, such as metal-ligand photocaging and photon up-conversion systems. However, these technologies require the use of a light-capturing sensitizer (Nani et al., 2015, Atilgan et al., 2014) or an expensive multi-photon light source (Brown et al., 1999, Tran et al., 2015). Recently, computational approaches have been used to develop a new family of quenching BODIPY dyes that can be decaged by exposure to green light. Upon exposure to green light, meso-substituted BODIPY fluorophores release acetic acid to restore fluorescence (Goswami et al., 2015, Rubinstein et al., 2015, Peterson et al., 2018). Unfortunately, this photoactivation mechanism utilizes the low excitation states of meso-substituted BODIPY analogs, a strategy that may not be easily applied to the design of other fluorophores. As such, there is a need for minimally-modified visible light-photoactivatable probes across a broad spectral range.

SUMMARY

In one aspect, the present disclosure provides photoactivatable fluorophores comprising a fluorophore core structure or an analog thereof and one or more thiocarbonyl groups, provided that the fluorophore core structure or analog thereof is not 2H-chromene or 4a,9,9a,10-tetrahydroacridine. In some embodiments, the fluorophore core structure is xanthene, acridine, phenoxazine, phenazine, dioxine, 2,3-dihydro-1H-indene, 2,3-dihydro-1H-inden-1-one, cyanine, pyrene, or an analog of any of these fluorophore core structures. In some embodiments, the fluorophore core structure is 2,3-dihydrophenalene, 2,3-dihydro-1H-phenalen-1-one, 1H-phenalene-1,3(2H)-dione, or 1,8-naphthalimide. In some embodiments, at least one of the one or more thiocarbonyl groups is in conjugation with the core structure.

In some embodiments, the photoactivatable fluorophore is further defined as:

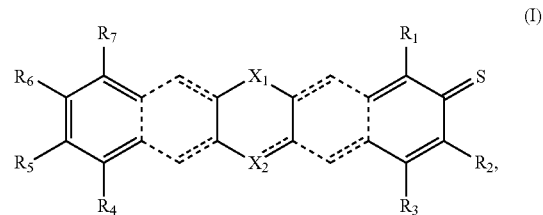

(I)

wherein:

$X_1$ is —O—, —S—, —C(O)—, —C(S)—, —NR$_a$—, or —Si(R$_u$)(R$_{u'}$)—, wherein:

R$_a$ is hydrogen, alkyl$_{(C \leq 8)}$, substituted alkyl$_{(C \leq 8)}$, acyl$_{(C \leq 8)}$, or substituted acyl$_{(C \leq 8)}$;

R$_u$ and R$_{u'}$ are each independently alkyl$_{(C \leq 8)}$, substituted alkyl$_{(C \leq 8)}$, aryl$_{(C \leq 12)}$, or substituted aryl$_{(C \leq 12)}$;

$X_2$ is —N=, —C(R$_b$)=, or —C(R$_c$)(R$_d$)— wherein:

R$_b$ is hydrogen; or alkyl$_{(C \leq 8)}$, substituted alkyl$_{(C \leq 8)}$, aryl$_{(C \leq 12)}$, or substituted aryl$_{(C \leq 12)}$;

R$_c$ and R$_d$ are taken together to form a group of the formula:

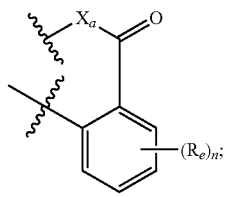

wherein:

n is 0, 1, 2, 3, or 4;

R$_e$ at each instance is independently hydrogen, halo, hydroxy, or amino; or alkyl$_{(C \leq 8)}$, alkoxy$_{(C \leq 8)}$, alkylamino$_{(C \leq 8)}$, dialkylamino$_{(C \leq 8)}$, or a substituted version of any of these groups; or $X_a$ is —O— or —$NR_f$—, wherein:
  $R_f$ is hydrogen; or
    alkyl$_{(C≤8)}$, substituted alkyl$_{(C≤8)}$, acyl$_{(C≤8)}$, or substituted acyl$_{(C≤8)}$; or
    —C(S)NH$R_g$, wherein:
      $R_g$ is alkyl$_{(C≤8)}$, substituted alkyl$_{(C≤8)}$, alkenyl$_{(C≤8)}$, or substituted alkenyl$_{(C≤8)}$;
$R_1$ is hydrogen, halo, hydroxy, amino, nitro, or cyano; or
  alkyl$_{(C≤8)}$, alkoxy$_{(C≤8)}$, alkylamino$_{(C≤8)}$, dialkylamino$_{(C≤8)}$, amido$_{(C≤8)}$, or a substituted version of any of these groups; or
  —C(O)$R_h$, wherein;
    $R_h$ is hydroxy or amino; or
      alkyl$_{(C≤8)}$, alkoxy$_{(C≤8)}$, alkylamino$_{(C≤8)}$, dialkylamino$_{(C≤8)}$, or a substituted version of any of these groups; and
$R_2$, $R_3$, $R_4$, $R_5$, $R_6$, and $R_7$ are each independently hydrogen, halo, hydroxy, amino, nitro, or cyano; or
  alkyl$_{(C≤8)}$, alkoxy$_{(C≤8)}$, alkylamino$_{(C≤8)}$, dialkylamino$_{(C≤8)}$, amido$_{(C≤8)}$, or a substituted version of any of these groups; or
  —C(O)$R_i$, wherein;
    $R_i$ is hydroxy or amino; or
      alkyl$_{(C≤8)}$, alkoxy$_{(C≤8)}$, alkylamino$_{(C≤8)}$, dialkylamino$_{(C≤8)}$, or a substituted version of any of these groups; or
$R_2$ and $R_3$, $R_4$ and $R_5$, $R_5$ and $R_6$, or $R_6$ and $R_7$ are taken together to form an arene$_{(C≤12)}$, a substituted arene$_{(C≤12)}$, a heteroarene$_{(C≤12)}$, or a substituted heteroarene$_{(C≤12)}$; or
a photoactivatable fluorophore of the formula:

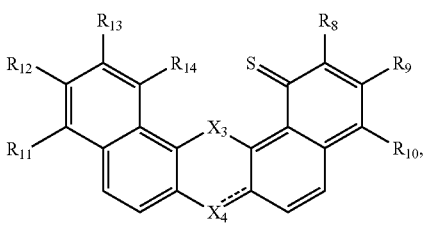

(II)

wherein:
  $X_3$ is —O—, —S—, —C(O)—, —C(S)—, —$NR_j$—, or —Si($R_v$)($R_{v'}$)—, wherein:
    $R_j$ is hydrogen, alkyl$_{(C≤8)}$, substituted alkyl$_{(C≤8)}$, acyl$_{(C≤8)}$, or substituted acyl$_{(C≤8)}$;
    $R_v$ and $R_{v'}$ are each independently alkyl$_{(C≤8)}$, substituted alkyl$_{(C≤8)}$, aryl$_{(C≤12)}$, or substituted aryl$_{(C≤12)}$;
  $X_4$ is —N=, —C($R_k$)=, or —C($R_l$)($R_m$)— wherein:
    $R_k$ is hydrogen; or
      alkyl$_{(C≤8)}$, substituted alkyl$_{(C≤8)}$, aryl$_{(C≤12)}$, or substituted aryl$_{(C≤12)}$;
    $R_l$ and $R_m$ are taken together to form a group of the formula:

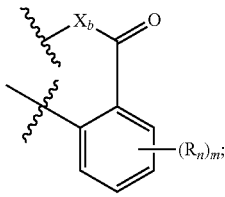

wherein:
  m is 0, 1, 2, 3, or 4;
  $R_n$ at each instance is independently hydrogen, halo, hydroxy, or amino; or
    alkyl$_{(C≤8)}$, alkoxy$_{(C≤8)}$, alkylamino$_{(C≤8)}$, dialkylamino$_{(C≤8)}$, or a substituted version of any of these groups; or
  $X_b$ is —O— or —$NR_o$—, wherein:
    $R_o$ is hydrogen; or
      alkyl$_{(C≤8)}$, substituted alkyl$_{(C≤8)}$, acyl$_{(C≤8)}$, or substituted acyl$_{(C≤8)}$; or
      —C(S)NH$R_p$, wherein:
        $R_p$ is alkyl$_{(C≤8)}$, substituted alkyl$_{(C≤8)}$, alkenyl$_{(C≤8)}$, or substituted alkenyl$_{(C≤8)}$;
$R_8$, $R_9$, $R_{10}$, $R_{11}$, $R_{12}$, $R_{13}$, and $R_{14}$ are each independently hydrogen, halo, hydroxy, amino, nitro, or cyano; or
  alkyl$_{(C≤8)}$, alkoxy$_{(C≤8)}$, alkylamino$_{(C≤8)}$, dialkylamino$_{(C≤8)}$, amido$_{(C≤8)}$, or a substituted version of any of these groups; or
  —C(O)$R_q$, wherein;
    $R_q$ is hydroxy or amino; or
      alkyl$_{(C≤8)}$, alkoxy$_{(C≤8)}$, alkylamino$_{(C≤8)}$, dialkylamino$_{(C≤8)}$, or a substituted version of any of these groups; or
$R_8$ and $R_9$, $R_9$ and $R_{10}$, $R_{11}$ and $R_{12}$, $R_{12}$ and $R_{13}$, or $R_{13}$ and $R_{14}$ are taken together to form an arene$_{(C≤12)}$, a substituted arene$_{(C≤12)}$, a heteroarene$_{(C≤12)}$, or a substituted heteroarene$_{(C≤12)}$; or
a photoactivatable fluorophore of the formula:

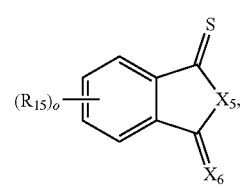

(III)

wherein:
  o is 0, 1, 2, 3, or 4;
  $X_5$ is —O— or —$NR_r$—, wherein:
    $R_r$ is hydrogen; or
      alkyl$_{(C≤8)}$, substituted alkyl$_{(C≤8)}$, acyl$_{(C≤8)}$, or substituted acyl$_{(C≤8)}$; or
      —C(O)$R_s$, wherein:
        $R_s$ is hydroxy or amino; or
          alkyl$_{(C≤8)}$, alkoxy$_{(C≤8)}$, alkylamino$_{(C≤8)}$, dialkylamino$_{(C≤8)}$, or a substituted version of any of these groups;
  $X_6$ is =O or =S; and
  $R_{15}$ at each instance is independently hydrogen, halo, hydroxy, amino, nitro, or cyano; or
    alkyl$_{(C≤8)}$, alkoxy$_{(C≤8)}$, alkylamino$_{(C≤8)}$, dialkylamino$_{(C≤8)}$, amido$_{(C≤8)}$, or a substituted version of any of these groups; or
    —C(O)$R_t$, wherein;
      $R_t$ is hydroxy or amino; or
        alkyl$_{(C≤8)}$, alkoxy$_{(C≤8)}$, alkylamino$_{(C≤8)}$, dialkylamino$_{(C≤8)}$, or a substituted version of any of these groups; or a photoactivatable fluorophore of the formula:

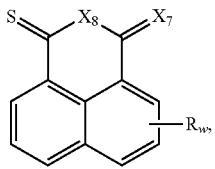
(X)

wherein:
- $X_7$ is O or S;
- $X_8$ is —O— or —$NR_x$—, wherein
  - $R_x$ is hydrogen or substituted alkyl$_{(C\leq8)}$; or
  - —$S_1$-$L_1$-$S_2$—$R_y$, wherein:
    - $S_1$ is a covalent bond, -alkanediyl$_{(C\leq8)}$-, or substituted -alkanediyl$_{(C\leq8)}$-;
    - $L_1$ is a covalent bond or —C(O)—, —C(O)O—, or —C(O)$NR_z$—, wherein:
      - $R_z$ is hydrogen, alkyl$_{(C\leq8)}$, or substituted alkyl$_{(C\leq8)}$; and
    - $S_2$ is a covalent bond or —(CH$_2$CH$_2$O)$_n$—, wherein n is from 0 to 10;
    - $R_y$ is alkyl$_{(C\leq8)}$ or substituted alkyl$_{(C\leq8)}$; and
- $R_w$ is amino, cyano, halo, hydrogen, hydroxy, or nitro; or alkyl$_{(C\leq8)}$, cycloalkyl$_{(C\leq8)}$, heterocycloalkyl$_{(C\leq8)}$ or a substituted version of any of these groups;

or a pharmaceutically acceptable salt or tautomer of any of these formulae.

In some embodiments, the photoactivatable fluorophore is further defined as:

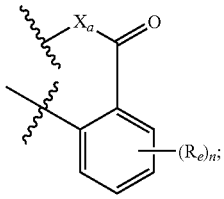
(I)

wherein:
- $X_1$ is —O—, —S—, —C(O)—, —C(S)—, or —$NR_a$—, wherein:
  - $R_a$ is hydrogen, alkyl$_{(C\leq8)}$, substituted alkyl$_{(C\leq8)}$, acyl$_{(C\leq8)}$, or substituted acyl$_{(C\leq8)}$;
- $X_2$ is —N═, —C($R_b$)═, or —C($R_c$)($R_d$)— wherein:
  - $R_b$ is hydrogen; or
    - alkyl$_{(C\leq8)}$, substituted alkyl$_{(C\leq8)}$, aryl$_{(C\leq12)}$, or substituted aryl$_{(C\leq12)}$;
  - $R_c$ and $R_d$ are taken together to form a group of the formula:

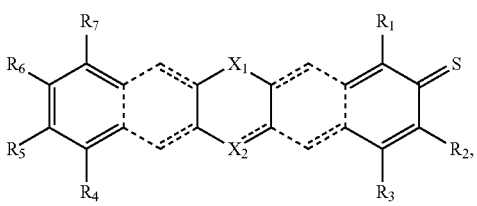

wherein:
- n is 0, 1, 2, 3, or 4;
- $R_e$ at each instance is independently hydrogen, halo, hydroxy, or amino; or
  - alkyl$_{(C\leq8)}$, alkoxy$_{(C\leq8)}$, alkylamino$_{(C\leq8)}$, dialkylamino$_{(C\leq8)}$, or a substituted version of any of these groups; or
- $X_a$ is —O— or —$NR_f$—, wherein:
  - $R_f$ is hydrogen; or
    - alkyl$_{(C\leq8)}$, substituted alkyl$_{(C\leq8)}$, acyl$_{(C\leq8)}$, or substituted acyl$_{(C\leq8)}$; or
    - —C(S)$NHR_g$, wherein:
      - $R_g$ is alkyl$_{(C\leq8)}$, substituted alkyl$_{(C\leq8)}$, alkenyl$_{(C\leq8)}$, or substituted alkenyl$_{(C\leq8)}$;
- $R_1$ is hydrogen, halo, hydroxy, amino, nitro, or cyano; or
  - alkyl$_{(C\leq8)}$, alkoxy$_{(C\leq8)}$, alkylamino$_{(C\leq8)}$, dialkylamino$_{(C\leq8)}$, amido$_{(C\leq8)}$, or a substituted version of any of these groups; or
  - —C(O)$R_h$, wherein;
    - $R_h$ is hydroxy or amino; or
      - alkyl$_{(C\leq8)}$, alkoxy$_{(C\leq8)}$, alkylamino$_{(C\leq8)}$, dialkylamino$_{(C\leq8)}$, or a substituted version of any of these groups; and
- $R_2$, $R_3$, $R_4$, $R_5$, $R_6$, and $R_7$ are each independently hydrogen, halo, hydroxy, amino, nitro, or cyano; or
  - alkyl$_{(C\leq8)}$, alkoxy$_{(C\leq8)}$, alkylamino$_{(C\leq8)}$, dialkylamino$_{(C\leq8)}$, amido$_{(C\leq8)}$, or a substituted version of any of these groups; or
  - —C(O)$R_i$, wherein;
    - $R_i$ is hydroxy or amino; or
      - alkyl$_{(C\leq8)}$, alkoxy$_{(C\leq8)}$, alkylamino$_{(C\leq8)}$, dialkylamino$_{(C\leq8)}$, or a substituted version of any of these groups; or
- $R_2$ and $R_3$, $R_4$ and $R_5$, $R_5$ and $R_6$, or $R_6$ and $R_7$ are taken together to form an arene$_{(C\leq12)}$, a substituted arene$_{(C\leq12)}$, a heteroarene$_{(C\leq12)}$, or a substituted heteroarene$_{(C\leq12)}$; or a photoactivatable fluorophore of the formula:

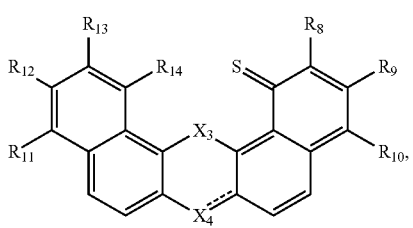
(II)

wherein:
- $X_3$ is —O—, —S—, —C(O)—, —C(S)—, or —$NR_j$—, wherein:
  - $R_j$ is hydrogen, alkyl$_{(C\leq8)}$, substituted alkyl$_{(C\leq8)}$, acyl$_{(C\leq8)}$, or substituted acyl$_{(C\leq8)}$;
- $X_4$ is —N═, —C($R_k$)═, or —C($R_l$)($R_m$)— wherein:
  - $R_k$ is hydrogen; or
    - alkyl$_{(C\leq8)}$, substituted alkyl$_{(C\leq8)}$, aryl$_{(C\leq12)}$, or substituted aryl$_{(C\leq12)}$;

R$_l$ and R$_m$ are taken together to form a group of the formula:

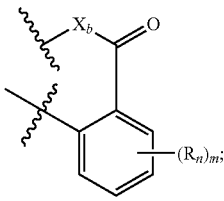

wherein:
m is 0, 1, 2, 3, or 4;
R$_n$ at each instance is independently hydrogen, halo, hydroxy, or amino; or
alkyl$_{(C\leq 8)}$, alkoxy$_{(C\leq 8)}$, alkylamino$_{(C\leq 8)}$, dialkylamino$_{(C\leq 8)}$, or a substituted version of any of these groups; or
X$_b$ is —O— or —NR$_o$—, wherein:
R$_o$ is hydrogen; or
alkyl$_{(C\leq 8)}$, substituted alkyl$_{(C\leq 8)}$, acyl$_{(C\leq 8)}$, or substituted acyl$_{(C\leq 8)}$; or
—C(S)NHR$_p$, wherein:
R$_p$ is alkyl$_{(C\leq 8)}$, substituted alkyl$_{(C\leq 8)}$, alkenyl$_{(C\leq 8)}$, or substituted alkenyl$_{(C\leq 8)}$;
R$_8$, R$_9$, R$_{10}$, R$_{11}$, R$_{12}$, R$_{13}$, and R$_{14}$ are each independently hydrogen, halo, hydroxy, amino, nitro, or cyano; or
alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
—C(O)R$_q$, wherein;
R$_q$ is hydroxy or amino; or
alkyl$_{(C\leq 8)}$, alkoxy$_{(C\leq 8)}$, alkylamino$_{(C\leq 8)}$, dialkylamino$_{(C\leq 8)}$, or a substituted version of any of these groups; or
R$_8$ and R$_9$, R$_9$ and R$_{10}$, R$_{11}$ and R$_{12}$, R$_{12}$ and R$_{13}$, or R$_{13}$ and R$_{14}$ are taken together to form an arene$_{(C\leq 12)}$, a substituted arene$_{(C\leq 12)}$, a heteroarene$_{(C\leq 12)}$, or a substituted heteroarene$_{(C\leq 12)}$; or a photoactivatable fluorophore of the formula:

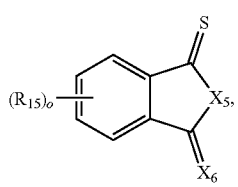

wherein:
o is 0, 1, 2, 3, or 4;
X$_5$ is —O— or —NR$_r$—, wherein:
R$_r$ is hydrogen; or
alkyl$_{(C\leq 8)}$, substituted alkyl$_{(C\leq 8)}$, acyl$_{(C\leq 8)}$, or substituted acyl$_{(C\leq 8)}$; or
—C(O)R$_s$, wherein:
R$_s$ is hydroxy or amino; or
alkyl$_{(C\leq 8)}$, alkoxy$_{(C\leq 8)}$, alkylamino$_{(C\leq 8)}$, dialkylamino$_{(C\leq 8)}$, or a substituted version of any of these groups;
X$_6$ is =O or =S; and
R$_{15}$ at each instance is independently hydrogen, halo, hydroxy, amino, nitro, or cyano; or
alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
—C(O)R$_t$, wherein;
R$_t$ is hydroxy or amino; or
alkyl$_{(C\leq 8)}$, alkoxy$_{(C\leq 8)}$, alkylamino$_{(C\leq 8)}$, dialkylamino$_{(C\leq 8)}$, or a substituted version of any of these groups;

or a pharmaceutically acceptable salt or tautomer of any of these formulae.

In further embodiments, the photoactivatable fluorophore is further defined as:

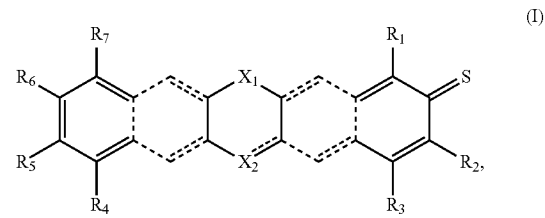

wherein:
X$_1$ is —O—, —S—, —C(O)—, —C(S)—, or —NR$_a$—, wherein:
R$_a$ is hydrogen, alkyl$_{(C\leq 8)}$, substituted alkyl$_{(C\leq 8)}$, acyl$_{(C\leq 8)}$, or substituted acyl$_{(C\leq 8)}$;
X$_2$ is —N=, —C(R$_b$)=, or —C(R$_c$)(R$_d$)— wherein:
R$_b$ is hydrogen; or
alkyl$_{(C\leq 8)}$, substituted alkyl$_{(C\leq 8)}$, aryl$_{(C\leq 12)}$, or substituted aryl$_{(C\leq 12)}$;
R$_c$ and R$_d$ are taken together to form a group of the formula:

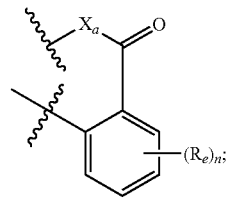

wherein:
n is 0, 1, 2, 3, or 4;
R$_e$ at each instance is independently hydrogen, halo, hydroxy, or amino; or
alkyl$_{(C\leq 8)}$, alkoxy$_{(C\leq 8)}$, alkylamino$_{(C\leq 8)}$, dialkylamino$_{(C\leq 8)}$, or a substituted version of any of these groups; or
X$_a$ is —O— or —NR$_f$—, wherein:
R$_f$ is hydrogen; or
alkyl$_{(C\leq 8)}$, substituted alkyl$_{(C\leq 8)}$, acyl$_{(C\leq 8)}$, or substituted acyl$_{(C\leq 8)}$; or
—C(S)NHR$_g$, wherein:
R$_g$ is alkyl$_{(C\leq 8)}$, substituted alkyl$_{(C\leq 8)}$, alkenyl$_{(C\leq 8)}$, or substituted alkenyl$_{(C\leq 8)}$;
R$_1$ is hydrogen, halo, hydroxy, amino, nitro, or cyano; or
alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
—C(O)R$_h$, wherein;
R$_h$ is hydroxy or amino; or alkyl$_{(C\leq 8)}$, alkoxy$_{(C\leq 8)}$, alkylamino$_{(C\leq 8)}$, dialkylamino$_{(C\leq 8)}$, or a substituted version of any of these groups; and $R_2$, $R_3$, $R_4$, $R_5$, $R_6$, and $R_7$ are each independently hydrogen, halo, hydroxy, amino, nitro, or cyano; or
  alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
  —C(O)R$_i$, wherein;
    R$_i$ is hydroxy or amino; or
      alkyl$_{(C\leq 8)}$, alkoxy$_{(C\leq 8)}$, alkylamino$_{(C\leq 8)}$, dialkylamino$_{(C\leq 8)}$, or a substituted version of any of these groups; or $R_2$ and $R_3$, $R_4$ and $R_5$, $R_5$ and $R_6$, or $R_6$ and $R_7$ are taken together to form an arene$_{(C\leq 12)}$, a substituted arene$_{(C\leq 12)}$, a heteroarene$_{(C\leq 12)}$, or a substituted heteroarene$_{(C\leq 12)}$;

or a pharmaceutically acceptable salt or tautomer thereof.

In still further embodiments, the photoactivatable fluorophore is further defined as:

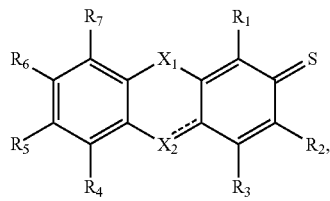

(IV)

wherein:
  $X_1$ is —O—, —S—, —C(O)—, —C(S)—, or —NR$_a$—, wherein:
    R$_a$ is hydrogen, alkyl$_{(C\leq 8)}$, substituted alkyl$_{(C\leq 8)}$, acyl$_{(C\leq 8)}$, or substituted acyl$_{(C\leq 8)}$;
  $X_2$ is —N=, —C(R$_b$)=, or —C(R$_c$)(R$_d$)— wherein:
    R$_b$ is hydrogen; or
      alkyl$_{(C\leq 8)}$, substituted alkyl$_{(C\leq 8)}$, aryl$_{(C\leq 12)}$, or substituted aryl$_{(C\leq 12)}$;
    R$_c$ and R$_d$ are taken together to form a group of the formula:

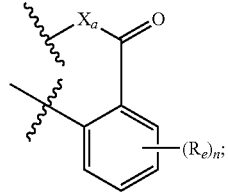

wherein:
  n is 0, 1, 2, 3, or 4;
  R$_e$ at each instance is independently hydrogen, halo, hydroxy, or amino; or
    alkyl$_{(C\leq 8)}$, alkoxy$_{(C\leq 8)}$, alkylamino$_{(C\leq 8)}$, dialkylamino$_{(C\leq 8)}$, or a substituted version of any of these groups; or
  X$_a$ is —O— or —NR$_f$—, wherein:
    R$_f$ is hydrogen; or
      alkyl$_{(C\leq 8)}$, substituted alkyl$_{(C\leq 8)}$, acyl$_{(C\leq 8)}$, or substituted acyl$_{(C\leq 8)}$; or —C(S)NHR$_g$, wherein:
  R$_g$ is alkyl$_{(C\leq 8)}$, substituted alkyl$_{(C\leq 8)}$, alkenyl$_{(C\leq 8)}$, or substituted alkenyl$_{(C\leq 8)}$;

$R_1$ is hydrogen, halo, hydroxy, amino, nitro, or cyano; or
  alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
  —C(O)R$_h$, wherein;
    R$_h$ is hydroxy or amino; or
      alkyl$_{(C\leq 8)}$, alkoxy$_{(C\leq 8)}$, alkylamino$_{(C\leq 8)}$, dialkylamino$_{(C\leq 8)}$, or a substituted version of any of these groups; and $R_2$, $R_3$, $R_4$, $R_5$, $R_6$, and $R_7$ are each independently hydrogen, halo, hydroxy, amino, nitro, or cyano; or
  alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
  —C(O)R$_i$, wherein;
    R$_i$ is hydroxy or amino; or
      alkyl$_{(C\leq 8)}$, alkoxy$_{(C\leq 8)}$, alkylamino$_{(C\leq 8)}$, dialkylamino$_{(C\leq 8)}$, or a substituted version of any of these groups; or $R_2$ and $R_3$, $R_4$ and $R_5$, $R_5$ and $R_6$, or $R_6$ and $R_7$ are taken together to form an arene$_{(C\leq 12)}$, a substituted arene$_{(C\leq 12)}$, a heteroarene$_{(C\leq 12)}$, or a substituted heteroarene$_{(C\leq 12)}$;

or a pharmaceutically acceptable salt or tautomer thereof.

In yet further embodiments, the photoactivatable fluorophore is further defined as:

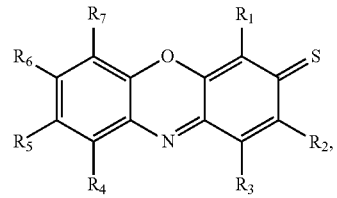

(V)

wherein:
  $R_1$ is hydrogen, halo, hydroxy, amino, nitro, or cyano; or
    alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
    —C(O)R$_h$, wherein;
      R$_h$ is hydroxy or amino; or
        alkyl$_{(C\leq 8)}$, alkoxy$_{(C\leq 8)}$, alkylamino$_{(C\leq 8)}$, dialkylamino$_{(C\leq 8)}$, or a substituted version of any of these groups; and $R_2$, $R_3$, $R_4$, $R_5$, $R_6$, and $R_7$ are each independently hydrogen, halo, hydroxy, amino, nitro, or cyano; or
  alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
  —C(O)R$_i$, wherein;
    R$_i$ is hydroxy or amino; or
      alkyl$_{(C\leq 8)}$, alkoxy$_{(C\leq 8)}$, alkylamino$_{(C\leq 8)}$, dialkylamino$_{(C\leq 8)}$, or a substituted version of any of these groups; or $R_2$ and $R_3$, $R_4$ and $R_5$, $R_5$ and $R_6$, or $R_6$ and $R_7$ are taken together to form an arene$_{(C\leq 12)}$, a substituted arene$_{(C\leq 12)}$, a heteroarene$_{(C\leq 12)}$, or a substituted heteroarene$_{(C\leq 12)}$;

or a pharmaceutically acceptable salt or tautomer thereof.

In further embodiments, the photoactivatable fluorophore is further defined as:

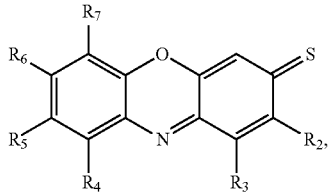

(VI)

wherein:
$R_2$ and $R_3$ are taken together to form an arene$_{(C \leq 12)}$, a substituted arene$_{(C \leq 12)}$, a heteroarene$_{(C \leq 12)}$, or a substituted heteroarene$_{(C \leq 12)}$; and
$R_4$, $R_5$, $R_6$, and $R_7$ are each independently hydrogen, halo, hydroxy, amino, nitro, or cyano; or
alkyl$_{(C \leq 8)}$, alkoxy$_{(C \leq 8)}$, alkylamino$_{(C \leq 8)}$, dialkylamino$_{(C \leq 8)}$, amido$_{(C \leq 8)}$, or a substituted version of any of these groups; or
—C(O)R$_i$, wherein;
$R_i$ is hydroxy or amino; or
alkyl$_{(C \leq 8)}$, alkoxy$_{(C \leq 8)}$, alkylamino$_{(C \leq 8)}$, dialkylamino$_{(C \leq 8)}$, or a substituted version of any of these groups; or
$R_4$ and $R_5$, $R_5$ and $R_6$, or $R_6$ and $R_7$ are taken together to form an arene$_{(C \leq 12)}$, a substituted arene$_{(C \leq 12)}$, a heteroarene$_{(C \leq 12)}$, or a substituted heteroarene$_{(C \leq 12)}$;
or a pharmaceutically acceptable salt or tautomer thereof.

In still further embodiments, the photoactivatable fluorophore is further defined as:

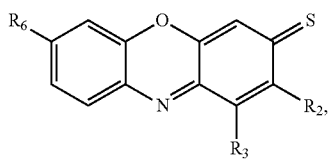

(VII)

wherein:
$R_2$ and $R_3$ are taken together to form an arene$_{(C \leq 12)}$, a substituted arene$_{(C \leq 12)}$, a heteroarene$_{(C \leq 12)}$, or a substituted heteroarene$_{(C \leq 12)}$; and
$R_6$ is hydrogen, halo, hydroxy, amino, nitro, or cyano; or
alkyl$_{(C \leq 8)}$, alkoxy$_{(C \leq 8)}$, alkylamino$_{(C \leq 8)}$, dialkylamino$_{(C \leq 8)}$, amido$_{(C \leq 8)}$, or a substituted version of any of these groups; or
—C(O)R$_i$, wherein;
$R_i$ is hydroxy or amino; or
alkyl$_{(C \leq 8)}$, alkoxy$_{(C \leq 8)}$, alkylamino$_{(C \leq 8)}$, dialkylamino$_{(C \leq 8)}$, or a substituted version of any of these groups;
or a pharmaceutically acceptable salt or tautomer thereof.

In some embodiments, $X_3$ is —Si(R$_v$)(R$_{v'}$)—. In some embodiments, $X_1$ is —Si(R$_u$)(R$_{u'}$)—.

In some embodiments, $R_2$ and $R_3$ are taken together to form an arene$_{(C \leq 12)}$ or a substituted arene$_{(C \leq 12)}$. In further embodiments, $R_2$ and $R_3$ are taken together to form an arene$_{(C \leq 12)}$, such as benzene. In some embodiments, $R_6$ is hydroxy, amino, alkylamino$_{(C \leq 8)}$, substituted alkylamino$_{(C \leq 8)}$, dialkylamino$_{(C \leq 8)}$, substituted dialkylamino$_{(C \leq 8)}$, amido$_{(C \leq 8)}$, or substituted amido$_{(C \leq 8)}$. In further embodiments, $R_6$ is amino, alkylamino$_{(C \leq 8)}$, dialkylamino$_{(C \leq 8)}$, or amido$_{(C \leq 8)}$. In still further embodiments, $R_6$ is dialkylamino$_{(C \leq 8)}$, such as diethylamino.

In other embodiments, the photoactivatable fluorophore is further defined as:

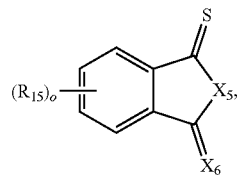

(III)

wherein:
o is 0, 1, 2, 3, or 4;
$X_5$ is —O— or —NR$_r$—, wherein:
$R_r$ is hydrogen; or
alkyl$_{(C \leq 8)}$, substituted alkyl$_{(C \leq 8)}$, acyl$_{(C \leq 8)}$, or substituted acyl$_{(C \leq 8)}$; or
—C(O)R$_s$, wherein:
$R_s$ is hydroxy or amino; or
alkyl$_{(C \leq 8)}$, alkoxy$_{(C \leq 8)}$, alkylamino$_{(C \leq 8)}$, dialkylamino$_{(C \leq 8)}$, or a substituted version of any of these groups;
$X_6$ is =O or =S; and
$R_{15}$ at each instance is independently hydrogen, halo, hydroxy, amino, nitro, or cyano; or
alkyl$_{(C \leq 8)}$, alkoxy$_{(C \leq 8)}$, alkylamino$_{(C \leq 8)}$, dialkylamino$_{(C \leq 8)}$, amido$_{(C \leq 8)}$, or a substituted version of any of these groups; or
—C(O)R$_t$, wherein;
$R_t$ is hydroxy or amino; or
alkyl$_{(C \leq 8)}$, alkoxy$_{(C \leq 8)}$, alkylamino$_{(C \leq 8)}$, dialkylamino$_{(C \leq 8)}$, or a substituted version of any of these groups;
or a pharmaceutically acceptable salt or tautomer thereof.

In further embodiments, the photoactivatable fluorophore is further defined as:

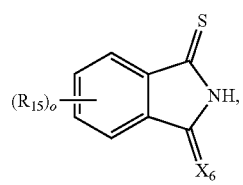

(VIII)

wherein:
o is 0, 1, 2, 3, or 4;
$X_6$ is =O or =S; and
$R_{15}$ at each instance is independently hydrogen, halo, hydroxy, amino, nitro, or cyano; or
alkyl$_{(C \leq 8)}$, alkoxy$_{(C \leq 8)}$, alkylamino$_{(C \leq 8)}$, dialkylamino$_{(C \leq 8)}$, amido$_{(C \leq 8)}$, or a substituted version of any of these groups; or
—C(O)R$_t$, wherein;
$R_t$ is hydroxy or amino; or
alkyl$_{(C \leq 8)}$, alkoxy$_{(C \leq 8)}$, alkylamino$_{(C \leq 8)}$, dialkylamino$_{(C \leq 8)}$, or a substituted version of any of these groups;
or a pharmaceutically acceptable salt or tautomer thereof.

In still further embodiments, the photoactivatable fluorophore is further defined as:

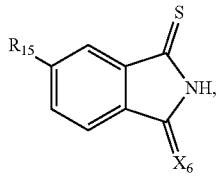

(IX)

wherein:
X$_6$ is =O or =S; and
R$_{15}$ is hydrogen, halo, hydroxy, amino, nitro, or cyano; or
    alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
    —C(O)R$_t$, wherein;
        R$_t$ is hydroxy or amino; or
            alkyl$_{(C\leq 8)}$, alkoxy$_{(C\leq 8)}$, alkylamino$_{(C\leq 8)}$, dialkylamino$_{(C\leq 8)}$, or a substituted version of any of these groups;
or a pharmaceutically acceptable salt or tautomer thereof.

In some embodiments, X$_6$ is =O. In other embodiments, X$_6$ is =S. In some embodiments, R$_{15}$ is hydrogen, hydroxy, amino, alkylamino$_{(C\leq 8)}$, substituted alkylamino$_{(C\leq 8)}$, dialkylamino$_{(C\leq 8)}$, substituted dialkylamino$_{(C\leq 8)}$, amido$_{(C\leq 8)}$, or substituted amido$_{(C\leq 8)}$. In further embodiments, R$_{15}$ is amino, alkylamino$_{(C\leq 8)}$, dialkylamino$_{(C\leq 8)}$, or amido$_{(C\leq 8)}$. In still further embodiments, R$_{15}$ is dialkylamino$_{(C\leq 8)}$, such as dimethylamino.

In other embodiments, R$_{15}$ is hydrogen.

In some embodiments, the photoactivatable fluorophore is further defined as:

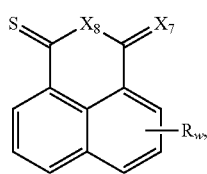

(X)

wherein:
X$_7$ is O or S;
X$_8$ is —O— or —NR$_x$—, wherein
    R$_x$ is hydrogen or substituted alkyl$_{(C\leq 8)}$; or
    —S$_1$-L$_1$-S$_2$—R$_y$, wherein:
        S$_1$ is a covalent bond, -alkanediyl$_{(C\leq 8)}$-, or substituted -alkanediyl$_{(C\leq 8)}$-;
        L$_1$ is a covalent bond or —C(O)—, —C(O)O—, or —C(O)NR$_z$—, wherein:
            R$_z$ is hydrogen, alkyl$_{(C\leq 8)}$, or substituted alkyl$_{(C\leq 8)}$; and
        S$_2$ is a covalent bond or —(CH$_2$CH$_2$O)$_n$—, wherein n is from 0 to 10;
        R$_y$ is alkyl$_{(C\leq 8)}$ or substituted alkyl$_{(C\leq 8)}$; and
    R$_w$ is amino, cyano, halo, hydrogen, hydroxy, or nitro; or alkyl$_{(C\leq 8)}$, cycloalkyl$_{(C\leq 8)}$, heterocycloalkyl$_{(C\leq 8)}$ or a substituted version of any of these groups;
or a pharmaceutically acceptable salt or tautomer thereof.

In some embodiments, the photoactivatable fluorophore is further defined as:

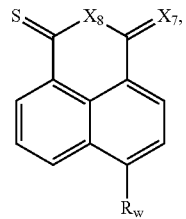

(XI)

wherein:
X$_7$ is O or S;
X$_8$ is —O— or —NR$_x$—, wherein
    R$_x$ is hydrogen or substituted alkyl$_{(C\leq 8)}$; or
    —S$_1$-L$_1$-S$_2$—R$_y$, wherein:
        S$_1$ is a covalent bond, -alkanediyl$_{(C\leq 8)}$-, or substituted -alkanediyl$_{(C\leq 8)}$-;
        L$_1$ is a covalent bond or —C(O)—, —C(O)O—, or —C(O)NR$_z$—, wherein:
            R$_z$ is hydrogen, alkyl$_{(C\leq 8)}$, or substituted alkyl$_{(C\leq 8)}$; and
        S$_2$ is a covalent bond or —(CH$_2$CH$_2$O)$_n$—, wherein n is from 0 to 10;
        R$_y$ is alkyl$_{(C\leq 8)}$ or substituted alkyl$_{(C\leq 8)}$; and
    R$_w$ is heterocycloalkyl$_{(C\leq 8)}$ or substituted heterocycloalkyl$_{(C\leq 8)}$;
or a pharmaceutically acceptable salt or tautomer thereof.

In some embodiments, R$_w$ is heterocycloalkyl$_{(C\leq 8)}$, such as N-pyrrolidinyl. In some embodiments, S$_1$ is -alkanediyl$_{(C\leq 8)}$-, such as —CH$_2$—. In some embodiments, R$_z$ is hydrogen. In some embodiments, n is 2. In some embodiments, R$_y$ is substituted alkyl$_{(C\leq 8)}$, such as 1-chlorohex-6-yl.

In some embodiments, the photoactivatable fluorophore is further defined as:

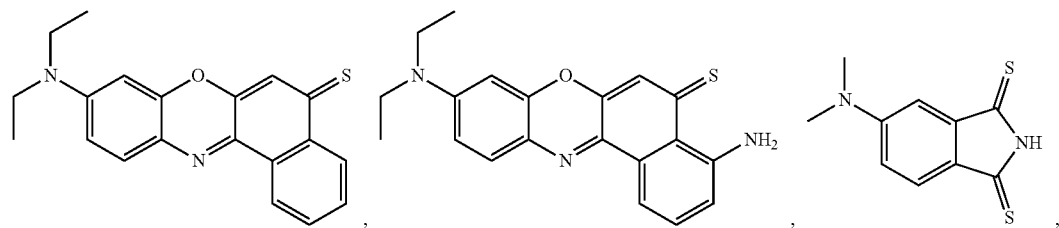

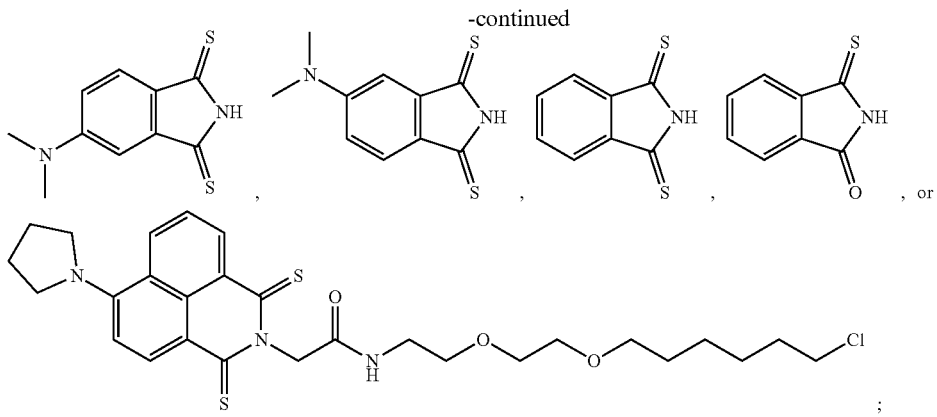

or a pharmaceutically acceptable salt or tautomer thereof.

In another aspect, the present disclosure provides conjugates of the formula:

T-L-E, wherein:
- E is a photoactivatable fluorophore according to any one of claims 1-31;
- L is a covalent bond or a linker; and
- T is a targeting moiety;

or a pharmaceutically acceptable salt thereof.

In some embodiments, L is a linker. In further embodiments, the linker is attached to E with an amide or an ester. In some embodiments, the linker is attached to T with an amide or an ester. In other embodiments, L is a covalent bond. In some embodiments, T is attached to E with an amide or an ester. In some embodiments, the targeting moiety is a nucleic acid sequence, a peptide, a protein, an antibody, an antibody fragment, a small molecule, or a functional group that targets one or more subcellular organelles.

In still another aspect, the present disclosure provides compositions comprising a photoactivatable fluorophore or conjugate of the present disclosure and an excipient. In some embodiments, the compositions are formulated for administration: intraarterially, intraarticularly, intracranially, intradermally, intralesionally, intramuscularly, intraocularly, intrapericardially, intraperitoneally, intrapleurally, intraprostatically, intrathecally, intratumorally, intraumbilically, intravenously, intravesicularlly, intravitreally, liposomally, locally, parenterally, subcutaneously, via injection, or via local delivery. In some embodiments, the composition is formulated as a unit dose.

In yet another aspect, the present disclosure provides methods of obtaining an image of a biological material contacted with a photoactivatable fluorophore, wherein the photoactivatable fluorophore comprises one or more thiocarbonyl groups, comprising irradiating the biological material with a first wavelength of light, wherein irradiating converts at least one of the one or more thiocarbonyl groups of the photoactivable fluorophore into a carbonyl group thereby producing a fluorophore, and performing fluorescence imaging to obtain an image of the biological material. In some embodiments, the photoactivatable fluorophore is a compound or conjugate of the present disclosure. In some embodiments, the biological material comprises $O_2$ or is in the presence of $O_2$. In some embodiments, the method is performed in vivo. In some embodiments, the method is performed on a patient. In further embodiments, is a mammal, such as a human.

In other embodiments, the method is performed ex vivo. In some embodiments, the biological material is a tissue sample. In some embodiments, the tissue sample is from a mammal, such as a human. In some embodiments, the biological material comprises a cell or a component of a cell. In further embodiments, the biological material comprises a cell, such as an adipocyte. In other embodiments, the biological material comprises a component of a cell. In further embodiments, the component of a cell is an organelle, such as a lipid droplet.

In some embodiments, the first wavelength of light is from about 300 nm to about 950 nm. In further embodiments, the first wavelength of light is from about 350 nm to about 750 nm. In still further embodiments, the first wavelength of light is from about 450 nm to about 650 nm. In yet further embodiments, the first wavelength of light is from about 450 nm to about 500 nm, such as about 488 nm. In other embodiments, the first wavelength of light is from about 600 nm to about 650 nm, such as about 615 nm. In some embodiments, the method further comprises photobleaching the fluorophore with a second wavelength of light. In some embodiments, the second wavelength of light is from about 200 nm to about 900 nm. In further embodiments, the second wavelength of light is from about 500 nm to about 600 nm, such as about 561 nm. In some embodiments, the fluorescence imaging uses the PALM or STORM method. In some embodiments, the fluorophore has a quantum yield greater than that of the photoactivatable fluorophore. In some embodiments, the fluorophore has a fluorescence intensity more than about 2-fold greater than the fluorescence intensity of the photoactivatable fluorophore. In further embodiments, the fluorophore has a fluorescence intensity more than about 4-fold greater than the fluorescence intensity of the photoactivatable fluorophore. In some embodiments, the photoactivatable fluorophore has an extinction coefficient that is greater than the extinction coefficient of the fluorophore. In some embodiments, the method further comprises diagnosing a disease or disorder.

In yet another aspect, the present disclosure provides methods of preparing a photoactivatable fluorophore of the present disclosure comprising obtaining a fluorophore, wherein the fluorophore comprises one or more carbonyl groups, and contacting the fluorophore with a thionation reagent under conditions resulting in the replacement of at least one carbonyl group by a thiocarbonyl group, thereby providing the photoactivatable fluorophore. In some embodiments, the thionation reagent is 2,4-bis(4-methoxyphenyl)-1,3,2,4-dithiadiphosphetane-2,4-dithione or elemental sulfur. In some embodiments, contacting further comprises a solvent. In further embodiments, the solvent is an organic solvent, such as benzene. In some embodiments, the method further comprises heating. In further embodiments, heating is to from about 25° C. to about 100° C. In further embodiments, heating is to from about 50° C. to about 90° C., such as about 80° C.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

(FIG. 2A) overlay of $^1$H NMR spectra (6.2-8.8 ppm) of SNile Red taken at the indicated light irradiation time points (615 nm, 0.4 µW cm$^{-2}$). (FIG. 2B) Normalized absorbance spectra of Nile Red, SNile Red, and SNile Red after photoactivation. (FIG. 2C) Fluorescence spectra of SNile Red after light irradiation with varying duration. (FIG. 2D) Fluorescence change of SNile Red irradiated with different wavelengths of light (470 nm, 0.4 µW cm$^{-2}$; 615 nm, 0.4 µW cm$^{-2}$; 780 nm, 0.4 µW cm$^{-2}$). (FIG. 2E) Fluorescence change of SNile Red in the presence or absence of light, or oxygen. (FIG. 2F) Absorbance change of DPBF at 410 nm in the presence of SNile Red or MB in DCM after different irradiation times.

(FIG. 11B) A plot of the changes in relative intracellular fluorescence intensity of SNile Red during photoactivation and photobleaching in living adipocytes using a 488 and a 564 nm laser, respectively. (FIG. 11C) Confocal fluorescence images of living adipocytes using SNile Red after photoactivation and photobleaching. Scale bar: 20 µm.

(FIGS. 12B-12F) Sequential photoactivation of adipocytes (cells 1, 2, 3, 4 and 5) by irradiation at 405 nm (2%). Dashed lines indicate the cell of interests. Scale bar: 50 µm.

(FIG. 13B) A magnified region featuring a SNile Red labeled lipid droplets by super-resolution reconstruction via PALM localization of spontaneous reactivation fluorescent events. (FIG. 13C) A further magnification of a PALM reconstructed of pair of lipid droplets with (FIG. 13D) corresponding histogram plot of the localization accuracy of reconstructed molecules.

FIG. 19A shows cells treated with 5NP-Halo (10 µM) for 1 h. FIG. 19B shows enhanced fluorescence upon photoactivation of the 5NP-Halo-treated cells.

DESCRIPTION OF ILLUSTRATIVE EMBODIMENTS

Figure 1:
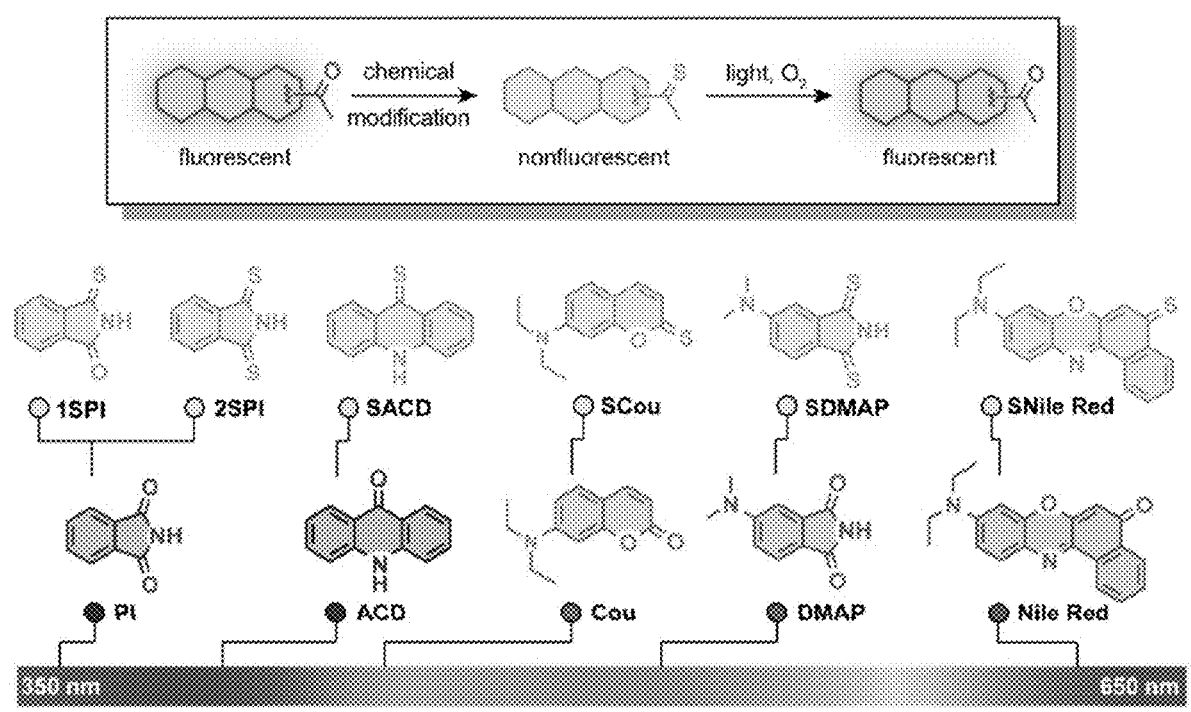
FIG. 1 shows the design of fluorogenic dyes (top). Thiocarbonyl substitution at the carbonyl group of fluorophores results in very weak fluorescence via a photoinduced electron transfer (PET)-quenching mechanism. Upon irradiation with light, the thiocarbonyl group can be efficiently desulfurized to its oxo derivative, thus restoring strong fluorescence of the fluorophores. Structures of thio-caged and uncaged fluorophores described in this disclosure (bottom).

In some aspects, the present disclosure provides photoactivatable fluorophores comprising one or more thiocarbonyl group as well as compositions and conjugates thereof. In another aspect, the present disclosure provides methods for the preparation the photoactivatable fluorophores disclosed herein. In still another aspect, the present disclosure provides methods of imaging comprising photoactivatable fluorophores comprising one or more thiocarbonyl group. These and other features are discussed further below.

I. PHOTOACTIVATABLE FLUOROPHORES

Non-limiting examples of the photoactivatable fluorophores of the present disclosure are shown below.

Structures of Photoactivatable Fluorophores

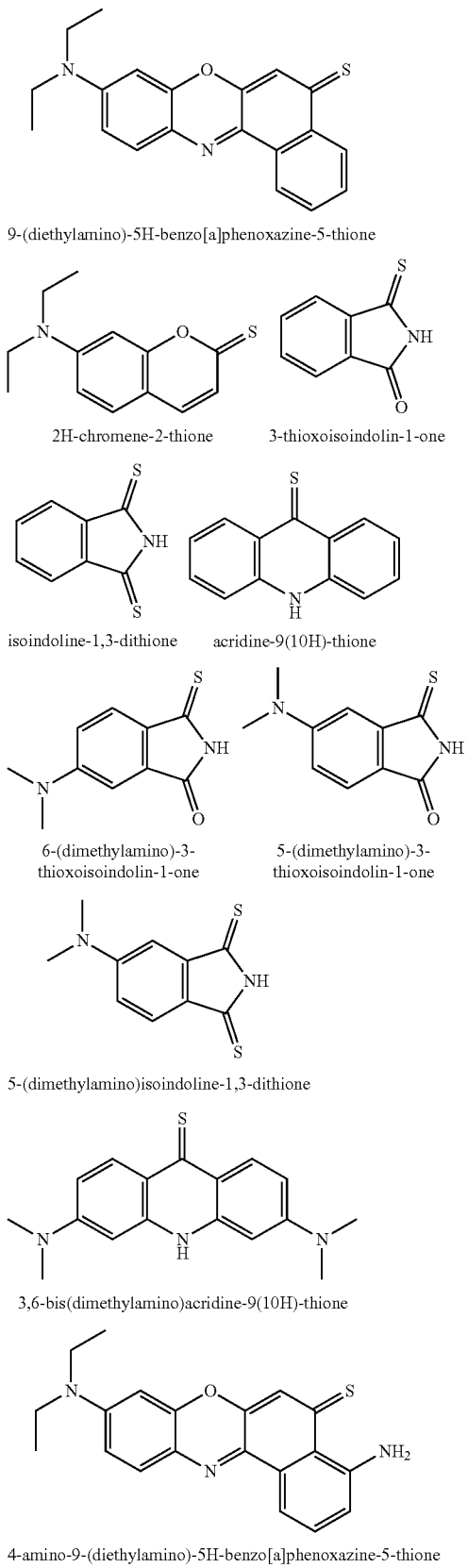

9-(diethylamino)-5H-benzo[a]phenoxazine-5-thione 2H-chromene-2-thione 3-thioxoisoindolin-1-one isoindoline-1,3-dithione acridine-9(10H)-thione 6-(dimethylamino)-3-thioxoisoindolin-1-one 5-(dimethylamino)-3-thioxoisoindolin-1-one 5-(dimethylamino)isoindoline-1,3-dithione 3,6-bis(dimethylamino)acridine-9(10H)-thione 4-amino-9-(diethylamino)-5H-benzo[a]phenoxazine-5-thione

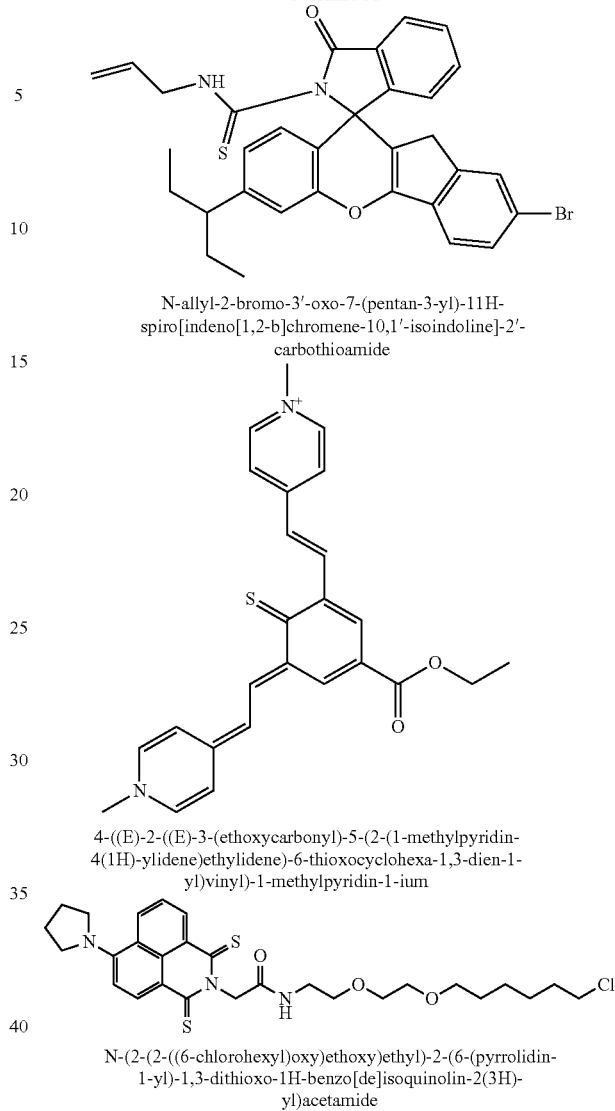

N-allyl-2-bromo-3'-oxo-7-(pentan-3-yl)-11H-spiro[indeno[1,2-b]chromene-10,1'-isoindoline]-2'-carbothioamide 4-((E)-2-((E)-3-(ethoxycarbonyl)-5-(2-(1-methylpyridin-4(1H)-ylidene)ethylidene)-6-thioxocyclohexa-1,3-dien-1-yl)vinyl)-1-methylpyridin-1-ium N-(2-(2-((6-chlorohexyl)oxy)ethoxy)ethyl)-2-(6-(pyrrolidin-1-yl)-1,3-dithioxo-1H-benzo[de]isoquinolin-2(3H)-yl)acetamide In some embodiments, the photoactivable fluorophore is 2-buty-6-(dimethylamino)-1H-benzo[de]isoquinoline-1,3 (2H)-dithione, 6-amino-2-butyl-1H-benzo[de]isoquinoline-1,3(2H)-dithione, 2-butyl-6-methoxy-1H-benzo[de]isoquinoline-1,3(2H)-dithione, 2-butyl-6-hydroxy-1H-benzo[de]isoquinoline-1,3(2H)-dithione, or 2-butyl-1H-benzo[de]isoquinoline-1,3(2H)-dithione.

Fluorophores are fluorescent chemical compounds that emit light upon excitation with a particular wavelength of light. Fluorophores typically comprise several aromatic groups and/or extended conjugation of π electrons within a planar molecule. Fluorophores may comprise aromatic groups alone or in conjugation with double bonds, such as alkenes or carbonyl groups, triple bonds, such as alkynes, or heteroatoms having lone pairs of electrons, such as oxygen, nitrogen, or sulfur. The aromatic groups may comprise heteroatoms, such as oxygen, nitrogen or sulfur. Many classes of fluorophores have been developed, including but not limited to fluoresceins, rhodamines, coumarins, cyanines, acridines, and acridones. All fluorophores that comprise at least one carbonyl group are envisioned in the context of the present disclosure.

The photoactivatable fluorophores of the present disclosure (also called the compounds of the present disclosure) are shown, for example, above, in the summary section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

In some embodiments, the compounds of the present invention have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present disclosure may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration. In some embodiments, the present compounds may contain two or more atoms which have a defined stereochemical orientation.

Chemical formulas used to represent compounds of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In some embodiments, compounds of the present disclosure exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

II. FLUOROPHORE CORE STRUCTURE

In some aspects, the present disclosure provides photoactivable fluorophores comprising a fluorophore core structure or an analog thereof and one or more thiocarbonyl groups. Fluorophores, i.e. fluorescent compounds, may have a core structure that comprises common structural characteristics, such as aromatic moieties, extended conjugation, and planarity. In some aspects, the present disclosure provides photoactivatable fluorophores comprising a fluorophore core structure or an analog thereof and one or more thiocarbonyl groups. In some embodiments, the fluorophore core structure comprises one or more aromatic rings. In some embodiments, the fluorophore core structure comprises two or more aromatic rings. When two or more aromatic rings are present, the two or more aromatic rings may each independently be fused or in conjugation with one another. In some embodiments, the fluorophore core structure comprises two or more aromatic rings that are fused. In some embodiments, the fluorophore core structure comprises two or more aromatic rings in conjugation. In some embodiments, the fluorophore core structure comprises two or more aromatic rings that are fused and one or more aromatic rings in conjugation with the two or more fused aromatic rings. In some embodiments, the two or more aromatic rings in conjugation are attached to one another with one or more heteroatoms, such as O, N, or S, and/or with an unsaturated carbon chain, such as an alkenediyl or alkynediyl group. In some embodiments, the entire fluorophore core structure is aromatic. In other embodiments, only a portion of the fluorophore core structure is aromatic. In some embodiments, the fluorophore core structure comprises one or more carbonyl groups. Non-limiting examples of fluorophore core structures include coumarin, bimane, 1,8-naphthalimide, 1,8-naphthalic anhydride, anthracene, acridine, acridin-2(9H)-one, xanthene, 9H-xanthen-9-one, 10H-phenoxazine, 3H-phenoxazin-3-one, benzofuran, isobenzofuran-1,3-dione, 2,3-dihydro-1H-indene, isoindoline-1,3-dione, 1H-isoindol-1-one, isoquinolin-1(2H)-one, 7H-benzo[c]xanthen-7-one, 5H-benzo[a]phenoxazin-5-one, 7H-dibenzo[c,h]phenoxazine, 1H-dibenzo[c,h]phenoxazin-1-one, fluorescein, or a cyanine, such as Cy3, Cy5, or Cy7.

One of skill in the art will recognize that analogs of the fluorophore core structures may be obtained by replacing one or more carbon atoms of the core structure with a heteroatom, such as O, N, or S. For example, isoindoline and isoindolin-1-one are analogs of 2,3-dihydro-1H-indene and 2,3-dihydro-1H-inden-1-one, respectively.

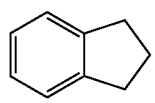

2,3-dihydro-1*H*-indene

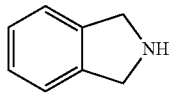

isoindoline

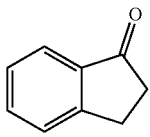

2,3-dihydro-1H-inden-1-one

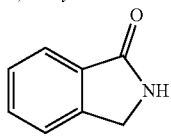

isoindolin-1-one

III. FLUORESCENCE QUENCHING

Fluorescence quenching can occur via different mechanisms, including Firster resonance energy transfer (FRET), photoinduced electron transfer (PET), and Dexter electron exchange (Dexter, 1953, Firster, 1959, Gould et al., 1994, Benelli et al., 2011). Among these mechanisms, PET is governed by redox chemistry and is not limited by spectral overlap between the donor and acceptor (Ueno et al., 2004 and Ceroni and Balzani, 2012), making it possible to use small-size caged groups to quench different fluorophores across a broad spectral range. The thiocarbonyl group may act as an effective fluorescence quencher for nearby fluorophores (Goldberg et al., 2010, 2012, 2013, Huang et al., 2016). Thioamides have been chemically incorporated into proteins as fluorescence quenchers to facilitate the study of protein dynamics, folding, and aggregation (Goldberg et al., 2010, 2012). This PET-quenching mechanism depends on the ability of the thioamide group to serve as an electron donor for the first excited singlet state of the fluorophore acceptor (Goldberg et al., 2013, Huang et al., 2016). Taking advantage of the PET-quenching mechanism, thiocoumarin probes have been developed for the detection of specific chemical species. In the presence of $Au^{3+}$, $Hg^{2+}$, or strong oxidizing agents, thiocoumarin derivatives with weak fluorescence signals may undergo oxidative desulfurization to their fluorescent oxo analogues (Choi et al., 2009, Moon et al., 2012, Park et al., 2012). The present disclosure provides methods for single atom substitution of fluorophores, sulfur-for-oxygen replacement, which may be a general mechanism to quench fluorophores via a PET-quenching mechanism (FIG. 1). Without wishing to be bound by any theory, as a result of the relatively large size of sulfur atom, the orbital overlap of thiocarbonyl group may not be as efficient as that of carbonyl group, thus leading to higher highest occupied molecular orbitals (HOMOs) and lower lowest unoccupied molecular orbitals (LUMOs). The changes of frontier molecular orbitals make it possible to induce a PET effect within thio-caged fluorophores, and consequently quench the fluorescence. On the other hand, these thio-caged fluorophores can be photochemically oxidized to their native forms, thus restoring their fluorescence. In the presence of UV light and oxygen, thioketones were reported to afford the corresponding carbonyl compounds (Coyle, 1985 and Corsaro and Pistara, 1998). It was envisioned that conjugating the thiocarbonyl group to a large conjugated system, e.g., fluorophores, may enable the oxidization of these thiocarbonyl groups using light in the visible region (FIG. 1).

The present disclosure provides methods for preparing photoactivatable fluorophores by replacing one or more oxygen atoms with one or more sulfur atoms within the fluorophores. It is found that introduction of a thiocarbonyl moiety into fluorophores leads to PET-induced fluorescence quenching, a state that is highly reversible by exposure to visible light and air. The superior activation efficiency of these photoactivatable fluorophores has enabled the use of super-resolution imaging to obtain ultrastructural information from subcellular organelles.

The photoactivatable fluorophores of the present disclosure comprise one or more thiocarbonyl groups. In some embodiments, the photoactivatable fluorophore comprises a fluorophore core structure or an analog thereof and one or more thiocarbonyl groups. Non-limiting examples of fluorophore cores structures include coumarin, bimane, 1,8-naphthalimide, 1,8-naphthalic anhydride, anthracene, acridine, acridin-2(9H)-one, xanthene, 9H-xanthen-9-one, 10H-phenoxazine, 3H-phenoxazin-3-one, benzofuran, isobenzofuran-1,3-dione, 2,3-dihydro-1H-indene, isoindoline-1,3-dione, 1H-isoindol-1-one, isoquinolin-1(2H)-one, 7H-benzo[c]xanthen-7-one, 5H-benzo[a]phenoxazin-5-one, 7H-dibenzo[c,h]phenoxazine, 1H-dibenzo[c,h]phenoxazin-1-one, fluorescein, or a cyanine, such as Cy3, Cy5, or Cy7. In some embodiments, the thiocarbonyl group is in conjugation with the fluorophore core structure. In other embodiments, the thiocarboyl group is not in conjugation with the fluorophore core structure. In some embodiments, the photoactivatable fluorophore is prepared from a fluorophore comprising at least one carbonyl group.

IV. PREPARATION AND USE OF PHOTOACTIVATABLE FLUOROPHORES

In some embodiments, the present disclosure provides methods of preparing photoactivatable fluorophores as well as methods of imaging therewith. Photoactivatable fluorophores are fluorophores that have been chemically modified to replace one or more carbonyl oxygen atoms with a sulfur. Replacement of the one of more carbonyl oxygen atoms for sulfur in the fluorophore may attenuate the fluorescence of the resulting photoactivatable fluorophore. Upon photoactivation comprising exposure to a wavelength of light of proper and sufficient energy in the presence of oxygen, the photoactivatable fluorophore undergoes a chemical transformation to replace at least one thiocarbonyl sulfur atom with an oxygen atom to afford a fluorophore. The fluorophore may have enhanced fluorescence compared with that of the photoactivatable fluorophore.

In some embodiments, the photoactivable fluorophores of the present disclosure comprise one or more thiocarbonyl group. In some embodiments, the photoactivatable fluorophore is prepared via chemical modification of a fluorophore comprising one or more carbonyl groups. In some embodiments, the chemical modification is thionation, wherein one or more carbonyl groups of the fluorophore are converted into one or more thiocarbonyl groups. In some embodiments, thionation is achieved upon contacting a fluorophore comprising one or more carbonyl groups with a thionation reagent under conditions sufficient to result in the conversion of the one or more carbonyl groups into one or more thiocarbonyl groups. One of skill in the art will recognize that there are many thionation reagents capable of converting carbonyl groups to thiocarbonyl groups, including but not limited to elemental sulfur, hydrogen sulfide (Molina et al., 1997), Lawesson's reagent (2,4-bis(4-methoxyphenyl)-1,3,2,4-dithiadiphosphetane-2,4-disulfide; Thomsen et al., 1990), Belleau's reagent, a Davy reagent, ammonium phosphorodithioate (Kaboudin and Malekzadeh, 2011), thiophosphoryl chloride (Pathak et al., 2008), $P_4S_{10}/(Me_3Si)_2O$ (Curphey, 2002), and $P_4S_{10}/Al_2O_3$(Polshettiwar and Kaushik, 2004). Any thionation reagent is considered to be within the scope of the present disclosure. In some embodiments, the fluorophore and the thionation reagent are contacted in a solvent, including but not limited to an organic solvent, such as benzene, toluene, xylene (any isomer or mixture thereof), dichloromethane, choroform, hexane, or an ethereal solvent. In some embodiments, the fluorophore and the thionation reagent may require heating to promote and/or accelerate the rate of thionation. In some embodiments, the thionation reaction may be performed at about room temperature or at a temperature selected from the range of about 20° C. to about 200° C., or any range derivable therein. In some embodiments, the thionation reaction may be performed at a temperature selected from the range from about 20° C. to about 100° C., such as 20° C., 30° C., 40° C., 50° C., 60° C., 70° C., 80° C., 90° C., or 100° C. In some embodiments, the thionation reaction is performed in a solvent that is heated to reflux.

The photoactivatable fluorophores of the present disclosure may be used for imaging. In some embodiments, the photoactivatable fluorophore is contacted with a biological sample, such as a cell (e.g., an adipocyte) or a component of a cell (e.g., an organelle, such as a lipid droplet). In some embodiments, the photoactivatable fluorophores are used in the imaging of proteins, lipids, RNA, DNA, small molecules. In some embodiments, imaging is performed in vivo, in vitro, or ex vivo. In some embodiments, irradiating the photoactivatable fluorophore with a first wavelength of light sufficient to convert one or more of the thiocarbonyl groups into a carbonyl group, produces a fluorophore. In some embodiments, irradiating the photoactivatable fluorophore with the first wavelength is performed in the presence of oxygen. Oxygen may be present within the biological sample and/or may be present in the atmosphere in which irradiation is performed. In some embodiments, the first wavelength of light is in the range from about 200 nm to about 950 nm or any range derivable therein. In some embodiments, the first wavelength of light is in the range from about 350 nm to about 750 nm. In some embodiments, the fluorophore that is produced upon irradiation of the photoactivable fluorophore is imaged via fluorescence imaging. In some embodiments, the fluorescence imaging comprises irradiating the fluorophore with a second wavelength of light and detecting a signal emitted by the fluorophore to produce an image. In some embodiments, imaging further comprises photobleaching. In some embodiments, the photoactivatable fluorophores may be used for super-resolution imaging, such as PALM or STORM.

V. TARGETING MOIETIES

In some aspects, the present disclosure provides compounds conjugated directly or through linkers to a targeting moiety. In some embodiments, the conjugation of the compound to a targeting moiety increases imaging selectivity. Non-limiting examples of targeting moieties include: antibodies, such as anti-epidermal growth factor receptor (EGFR) deletion mutant antibody or single chain antiprostate stem cell antigen (PSCA) antibody; peptides, such as chlorotoxin (CTX) or arginine-glycine-aspartic acid (RGD) peptide sequence; aptamers, such as pegaptanib or AS1411; small molecules, such as growth factors, hormones, cofactors, or cytokines (e.g. folic acid or flavin mononucleotide (FMN)); or functional groups that target subcellular organelles, such as morpholine to target lysosomes, triphenylphosphonium to target mitochondria, cysteine to target Golgi apparatus and phenyl sulfonamide to target endoplasmic reticulum. In some embodiments, the targeting moieties may bind one analyte (e.g. a particular cell type) selectively in the presence of a plurality of analytes.

In some embodiments, the targeting moiety may be a peptide sequence or a cyclic peptide. In some embodiments, targeting moieties are antibodies or avimers. Antibodies and avimers can be generated against virtually any cell surface marker thus, providing a method for targeted delivery of the compound to virtually any cell population of interest.

Additionally, it is contemplated that the compounds described herein may be conjugated to a nanoparticle or other nanomaterial. Some non-limiting examples of nanoparticles include metal nanoparticles such as gold or silver nanoparticles or polymeric nanoparticles such as poly-L-lactic acid or poly(ethylene) glycol polymers.

VI. FORMULATIONS AND ROUTES OF ADMINISTRATION

In another aspect, for administration to a patient for imaging, formulations (also referred to as compositions) comprise an effective amount of a compound disclosed herein formulated with one or more excipients and/or carriers appropriate to the indicated route of administration. In some embodiments, the compounds disclosed herein are formulated in a manner amenable for imaging human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the formulations may be subjected to pharmaceutical operations, such as sterilization, and/or may contain carriers and/or excipients such as preservatives, stabilizers, wetting agents, emulsifiers, encapsulating agents such as lipids, dendrimers, polymers, proteins such as albumin, nucleic acids, and buffers.

Formulations may be administered by a variety of methods, e.g., orally or by injection (e.g., subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Non-limiting examples of diluents include saline and aqueous buffer solutions. Non-limiting examples of liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient's diet. For oral administration, the compounds disclosed herein may be incorporated with excipients and used in the form of ingestible tablets, buccal tablets, troches, capsules, elixirs, suspensions, syrups, wafers, and the like. The percentage of the imaging compound in the compositions and preparations may, of course, be varied. The amount of the imaging compound in such formulations is such that a suitable dosage will be obtained.

The imaging compound may also be administered topically to the skin, eye, ear, or mucosal membranes. Administration of the imaging compound topically may include formulations of the compounds as a topical solution, lotion, cream, ointment, gel, foam, transdermal patch, or tincture. When the imaging compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the imaging compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of imaging compound calculated to produce the desired effect in association with the required carrier. In some embodiments, the specification for the dosage unit forms of the invention are dictated by and directly dependent on (a) the unique characteristics of the imaging compound and the particular imaging effect to be achieved, and (b) the limitations inherent in the art of compounding such a compound for imaging in a patient. In some embodiments, imaging compounds are administered at an effective dosage sufficient to produce an image. For example, the efficacy of a compound can be evaluated in an animal model system that may be predictive of efficacy in imaging a human or another animal. In some embodiments, the image produced may be used to diagnose, prognose, stage, or monitor the progression of a disease or disorder.

In some embodiments, the effective dose range for the imaging compound can be extrapolated from effective doses determined in animal studies for a variety of different animals. In some embodiments, the human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the imaging composition depend on the judgment of the practitioner and are specific to each individual. Nonetheless, a calculated HED dose provides a general guide. Other factors affecting the dose include the physical and clinical state of the patient, the route of administration, the intended goal of imaging and the potency, stability and toxicity of the particular imaging formulation.

The actual dosage amount of a compound of the present disclosure or composition comprising a compound of the present disclosure administered to a patient may be determined by physical and physiological factors such as type of animal treated, age, sex, body weight, severity of condition, the type of disease being imaged, previous or concurrent therapeutic interventions or imaging procedures, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the imaging compound in the formulation is from about 2 to about 75 weight percent. In some of these embodiments, the amount if from about 25 to about 60 weight percent.

Single or multiple doses of the imaging compounds or formulations are contemplated. Desired time intervals for delivery of multiple doses can be determined by one of ordinary skill in the art employing no more than routine experimentation. As an example, patients may be administered two doses daily at approximately 12-hour intervals. In some embodiments, the compound or formulation is administered once a day.

The compound(s) or formulation(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc.

VII. CHEMICAL DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "thiocarbonyl" means —C(=S)—; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, the formula

covers, for example,

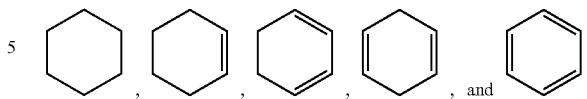

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ∿∿ ", when drawn perpendicularly across a bond (e.g.,

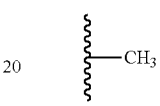

for methyl) indicates a point of attachment of the group. It is noted that the point of attachment is typically only identified in this manner for larger groups in order to assist the reader in unambiguously identifying a point of attachment. The symbol "◄■" means a single bond where the group attached to the thick end of the wedge is "out of the page." The symbol "⁞⁞⁞⁞", means a single bond where the group attached to the thick end of the wedge is "into the page". The symbol " ∿∿ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

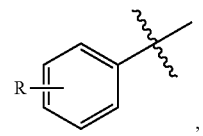

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

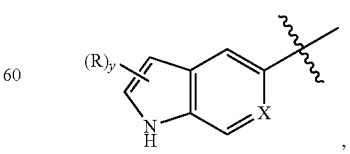

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/ groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

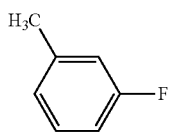

is also taken to refer to

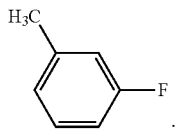

Aromatic compounds may also be depicted using a circle to represent the delocalized nature of the electrons in the fully conjugated cyclic π system, two non-limiting examples of which are shown below:

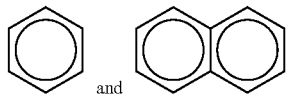

The term "alkyl" refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$(i-Pr, iPr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$(tert-butyl, t-butyl, t-Bu or $^t$Bu), and —CH$_2$C(CH$_3$)$_3$(neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$(cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

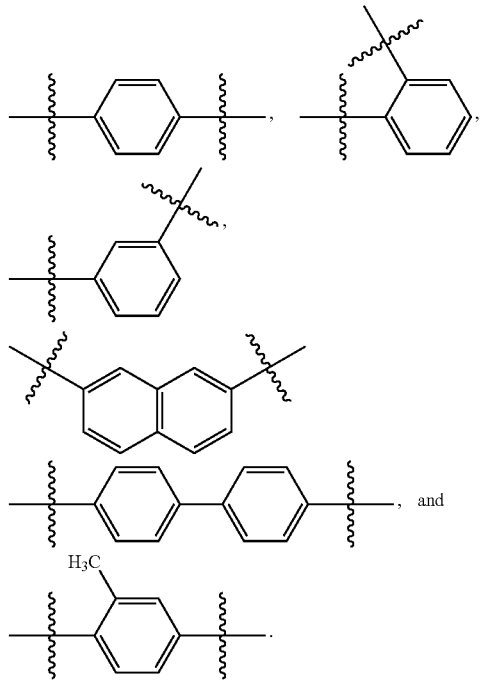

An "arene" refers to the class of compounds having the formula H—R, wherein R is aryl as that term is defined above. Benzene and toluene are non-limiting examples of arenes.

The term "aralkyl" refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl (Im), isoxazolyl, methylpyridinyl, oxazolyl, oxadiazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group.

The term "acyl" refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "alkoxy" refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$(isopropoxy), or —OC(CH$_3$)$_3$(tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

The term "alkylamino" refers to the group —NHR, in which R is an alkyl, as that term is defined above. Non-limiting examples include: —NHCH$_3$ and —NHCH$_2$CH$_3$. The term "dialkylamino" refers to the group —NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The terms "dicycloalkylamino", "dialkenylamino", "dialkynylamino", "diarylamino", "diaralkylamino", "diheteroarylamino", "diheterocycloalkylamino", and "dialkoxyamino", refers to groups, defined as —NRR', in which R and R' are both cycloalkyl, alkenyl, alkynyl, aryl, aralkyl, heteroaryl, heterocycloalkyl, and alkoxy, respectively. Similarly, the term alkyl(cycloalkyl)amino refers to a group defined as —NRR', in which R is alkyl and R' is cycloalkyl. The term "amido" (acylamino), when used without the "substituted" modifier, refers to the group —NHR, in which R is acyl, as that term is defined above. A non-limiting example of an amido group is —NHC(O)CH$_3$.

When a chemical group is used with the "substituted" modifier, one or more hydrogen atom has been replaced, independently at each instance, by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. For example, the following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups. Non-limiting examples of substituted aralkyls are: (3-chlorophenyl)-methyl, and 2-chloro-2-phenyl-eth-1-yl. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," when used in the context of imaging a patient or subject with a compound means that amount of the compound which, when administered to a subject or patient for imaging, is an amount sufficient to produce an image when the patient undergoes an imaging procedure, such as fluorescence imaging.

An "excipient" is a pharmaceutically acceptable substance formulated along with the active ingredient(s) of an imaging composition, formulation, or delivery system. Excipients may be used, for example, to stabilize the composition, to bulk up the composition (thus often referred to as "bulking agents," "fillers," or "diluents" when used for this purpose), or to confer an enhancement on the active ingredient in the final dosage form, such as facilitating absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

An "isomer" of a first compound is a separate compound in which each compound contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier" or simply "carrier" is a pharmaceutically acceptable substance formulated along with the imaging agent that is involved in carrying, delivering and/or transporting a chemical agent. Carriers may be used to improve the delivery and the effectiveness of imaging agents, including for example, controlled-release technology to modulate bioavailability, decrease metabolism, and/or reduce toxicity. Some carriers may increase the effectiveness of delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral compounds contain a chiral center, also referred to as a stereocenter or stereogenic center, which is any point, though not necessarily an atom, in a compound bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A compound can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Compounds with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

The present disclosure also includes the following abbreviations: DMSO, dimehtylsulfoxide; NMR, nuclear magnetic resonance; DPBF, 1,3-diphenylisobenzofuran; DCM, dichloromethane i.e., methylene chloride; PI, phthalimide; Cou, coumarin; ACD, acridone; 4-DMAP, 4-dimethylaminophthalimide; HOMO, highest-occupied molecular orbital; LUMO, lowest-unoccupied molecular orbital; DFT, density functional theory; CLSM, confocal laser scanning microscopy; DIC, differential interference contrast, PALM, photoactivatable localization microscopy; and STORM, stochastic optical reconstruction microscopy.

VIII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Discussion and Results

A. Results

Figures 2A, 2B, 2C, 2D, 2E, 2F:
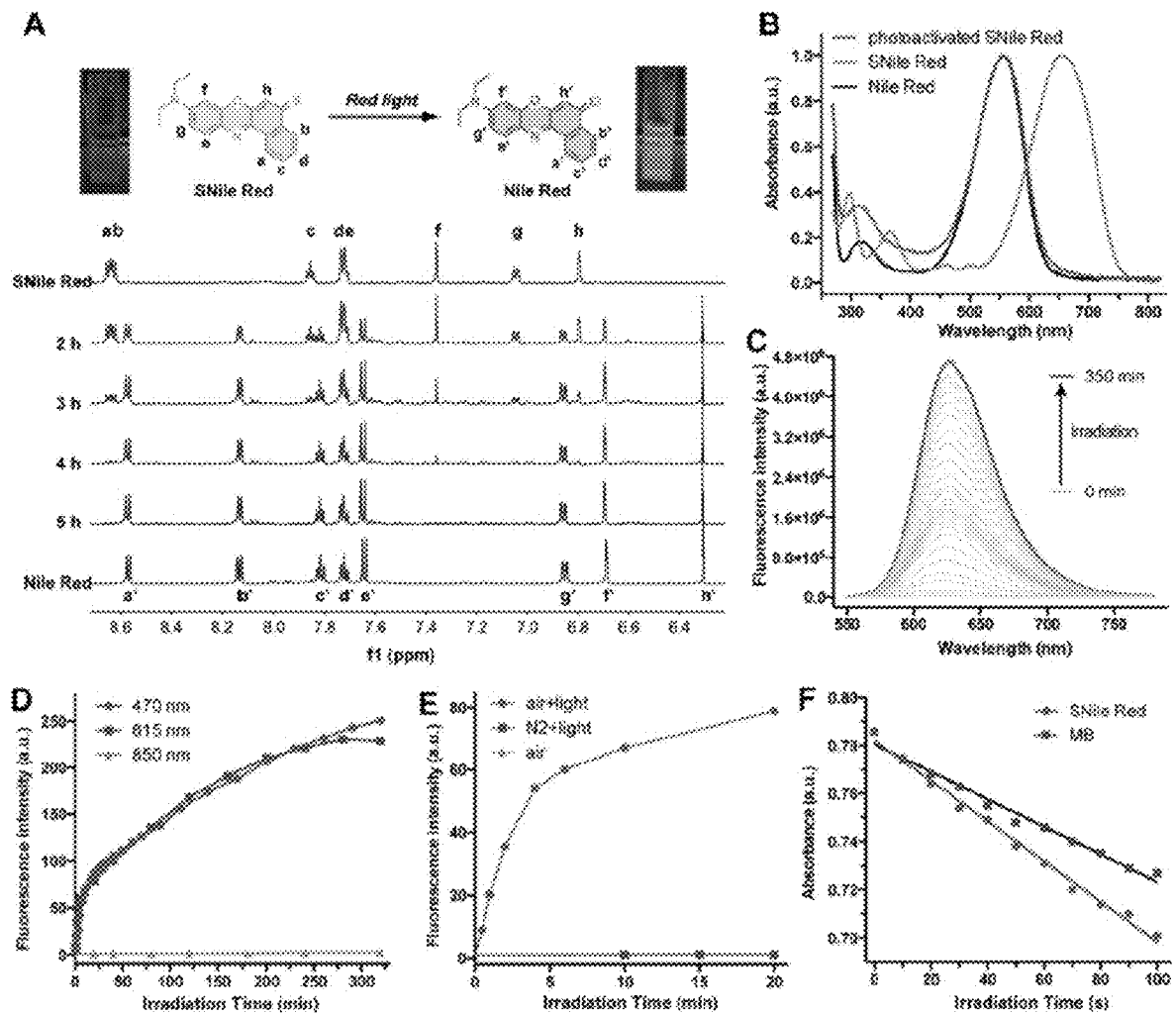
FIGS. 2A-F show.
Figure 3A:
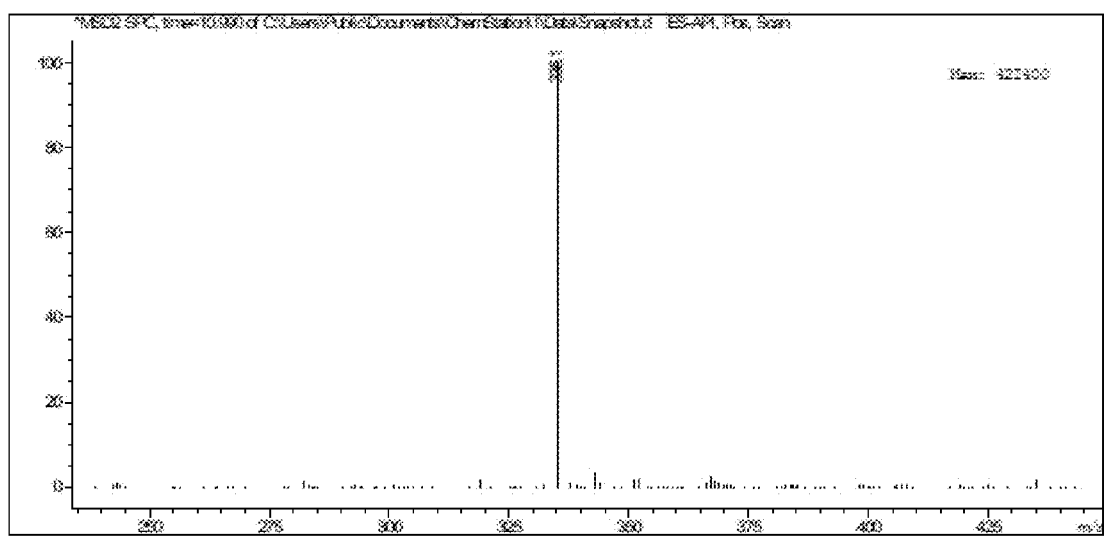
FIGS. 3A-B show ESI-Mass of SNile Red before (FIG. 3A) and after (FIG. 3B) irradiation.
Figure 3B:
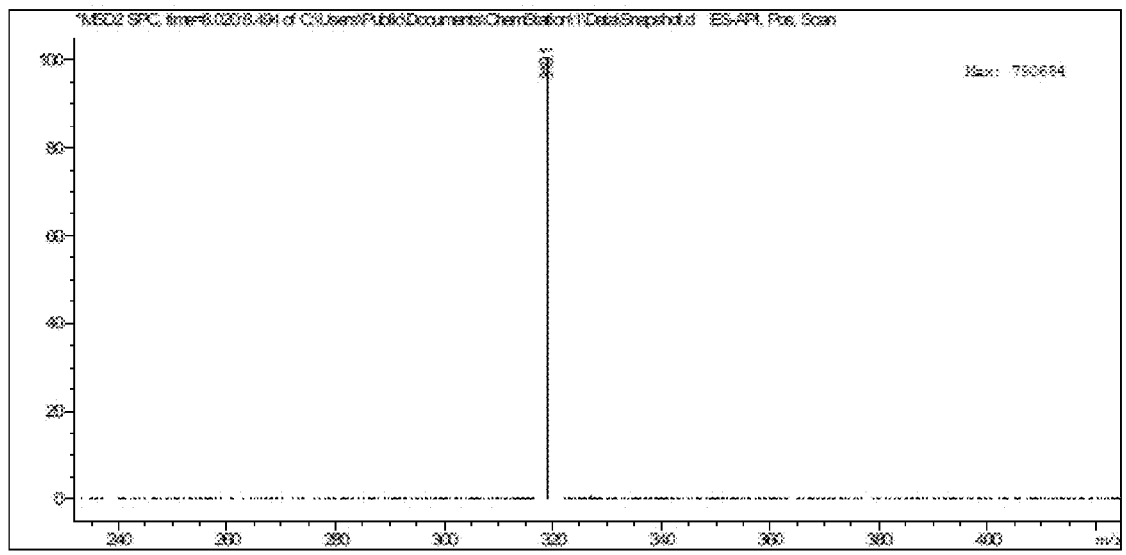
Figure 4:
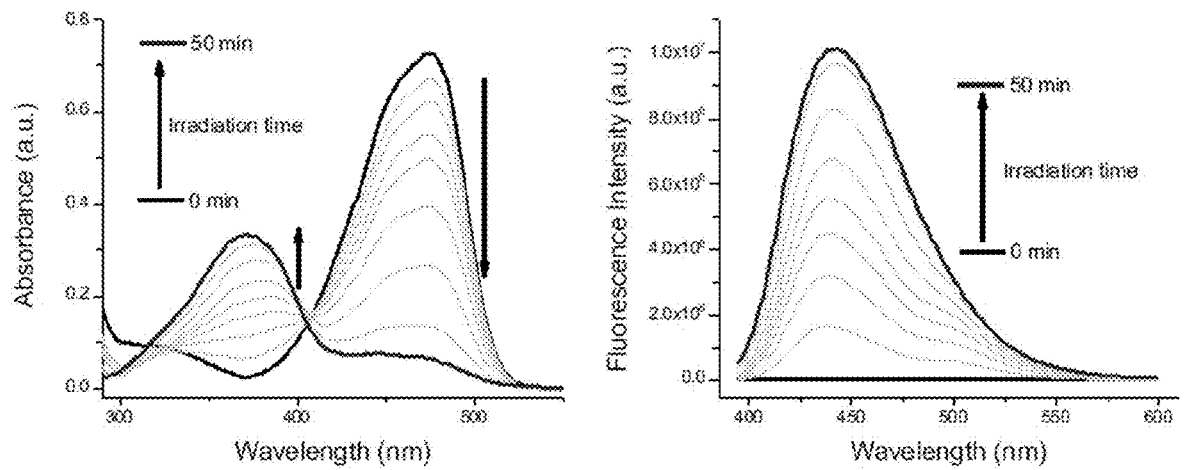
FIG. 4 shows photoactivation of SCou in DMSO by hand-held 365 nm lamp.
Figure 5:
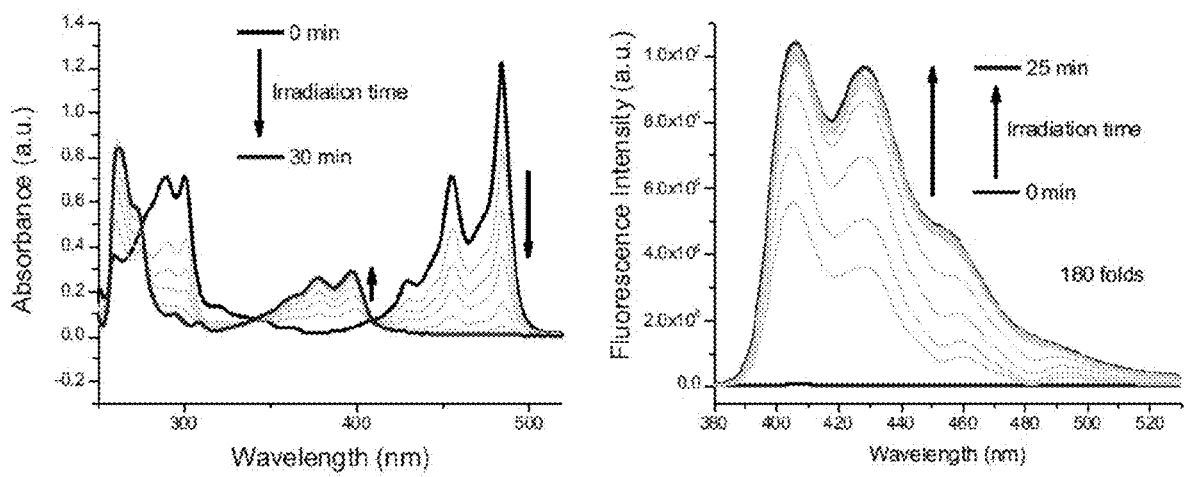
FIG. 5 shows photoactivation of SACD in DMSO by 470 nm.
Figure 6:
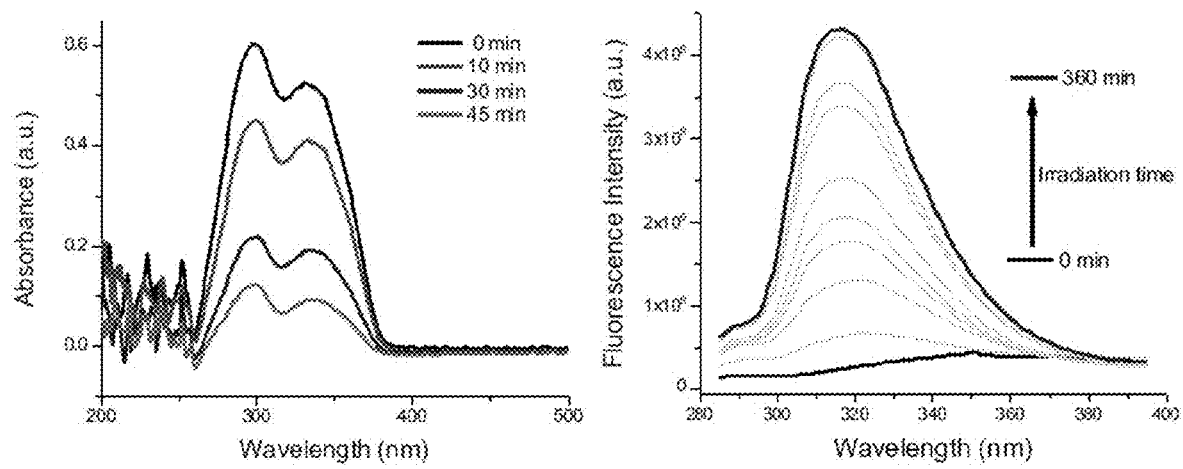
FIG. 6 shows photoactivation of 1SPI in DMSO by hand-held 365 nm lamp.
Figure 7:
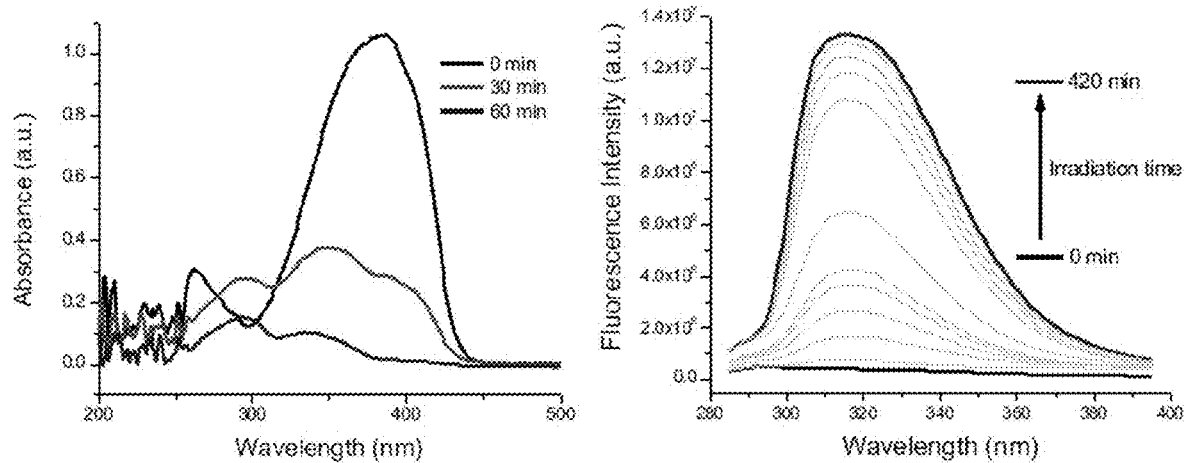
FIG. 7 shows photoactivation of 2SPI in DMSO by hand-held 365 nm lamp.
Figure 8:
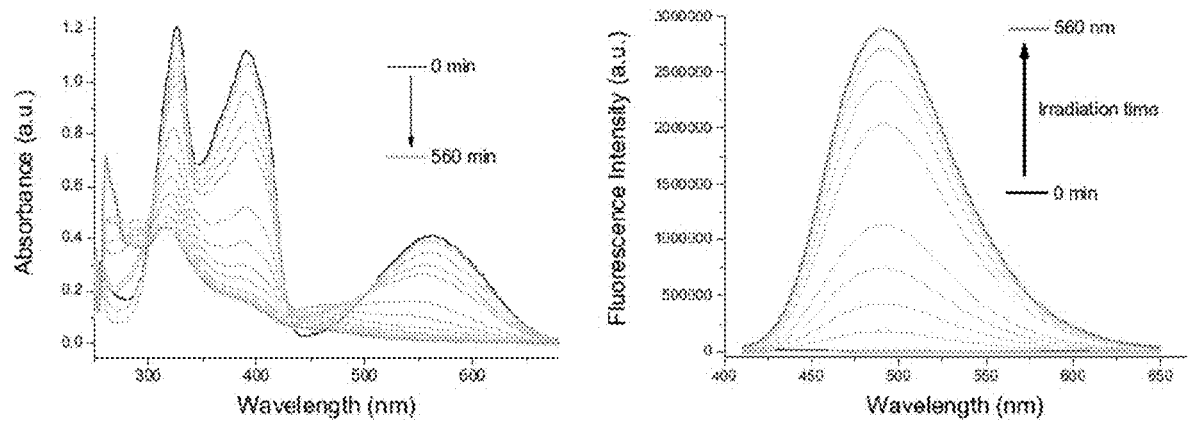
FIG. 8 shows photoactivation of SDMAP in DMSO by hand-held 365 nm lamp.

1. Thio-Caged Nile Red Synthesis and Characterization. To determine whether a minimal one atom sulfur-for-oxygen substitution within fluorophores can lead to fluorescence quenching, thio-caged Nile Red (SNile Red, FIG. 1) was synthesized, in which a carbonyl group was replaced with a thiocarbonyl moiety. Treatment of Nile Red with Lawesson's reagent in refluxing benzene produced the desired SNile Red in a yield of 40%. SNile Red in DMSO solution exhibited a strong absorption band at 652 nm, accompanied by weak fluorescence (FIG. 2A). The fluorescence quantum yield of SNile Red (ø<0.001) in DMSO is significantly lower than that of the Nile Red (ø=0.46), indicating the likelihood that the oxidizing desulfuration reaction could be used to re-activate the fluorescence of SNile Red (Table 1). Irradiation of SNile Red with red light (615 nm, 0.4 µW cm-2) led to the regeneration of fluorescent Nile Red in a high yield (FIG. 2A). The absorption maxima of SNile Red at 298, 368 and 652 nm were blue-shifted after desulfuration to 315 and 556 nm, in a good agreement with the absorption spectrum of authentic synthesized Nile Red (FIG. 2B). The A556/A652 value, representing the ratio of the absorbance maxima of Nile Red and SNile Red, increased from 0.25 to 30 after desulfuration reaction (FIG. 2B). Upon irradiation with red light, the fluorescence intensity of the desulfurated material at 626 nm increased 280-fold, accompanied by a change in fluorescence from dark to red (FIG. 2C). To evaluate the proper light source for SNile Red photoactivation, SNile Red was irradiated with either 470 nm, 615 nm, or 850 nm light for different times and fluorescence intensities at 626 nm were recorded. As shown in FIG. 2D, a significant fluorescence enhancement was observed with the light of shorter wavelengths than 652 nm, the maximum absorption wavelength of SNile Red. Treatment of light out of the absorbance range of SNile Red (850 nm), exhibited negligible activation of SNile Red after 5 hrs. These results demonstrated thio-caged fluorophores could be photoactivated using visible light source at the absorbance range of thio-caged dye other than the "always" UV light, which holds great promise for biological applications. To further characterize the photoactivated product of SNile Red, $^1$H NMR and ESI-MS spectral changes were measured in the process of photoactivation (FIG. 2A). Upon irradiation with red light (615 nm, 0.4 µW cm$^{-2}$), the aromatic protons exhibited an upfield shift. Signals corresponding to phenyl moiety protons at 8.64, 8.62, 7.85, 7.73, 7.36, 7.04, and 6.79 ppm gradually disappeared, and were replaced by new signals appearing at 8.57, 8.13, 7.81, 7.72, 7.63, 6.85, 6.69 and 6.30 ppm, respectively. After 5 hrs of irradiation, the $^1$H NMR spectrum of the final photoactivated product exhibited excellent agreement with that of Nile Red. The photoactivated product was also characterized by ESI-mass spectrometric analysis FIG. 3). The observed m/z 319.2 corresponding to Nile Red confirms the photoactivation product of SNile Red is its oxo form. Both dialkylthioketones and diarylthioketones are known to undergo photooxidation reaction under oxygen and light to give the corresponding ketones (Coyle, 1985, Corsaro and Pistara, 1998). To investigate the effects of dissolved oxygen and light on the photoactivation of thio-caged fluorophores, the time profile of the fluorescence of SNile Red was measured in the presence or absence of light, or oxygen. As shown in FIG. 2E, the fluorescence intensity at 626 nm increased 90-fold after irradiation with 615 nm light in air for 20 mins, while no change regarding the fluorescent spectrum was observed in the absence of light. To study the effect of oxygen during the photoactivation, the inventors prepared an oxygen-free SNile Red solution by bubbling nitrogen gas and irradiated at 615 nm. FIG. 2E shows that no significant change of fluorescence intensity was observed within 20 mins irradiation without oxygen. Inspired by the photoactivation mechanism of thioketones, it was hypothesized that singlet oxygen generated by self-sensitization can be the active species to oxidize thiocarbonyl groups within fluorophores (Coyle, 1985 and Corsaro and Pistara, 1998). To prove this, 1,3-diphenylisobenzofuran (DPBF), a classical singlet oxygen detection reagent, was used to determine the involvement of singlet oxygen in these oxidative reactions (Spiller et al., 1998 and Tang et al., 2013). As shown in FIG. 2F, the singlet oxygen generation was confirmed by the absorbance decrease of DPBF at 410 nm in methylene dichloride (DCM) during light irradiation (615/30 nm). The singlet oxygen quantum yield (DA) was further determined to be 0.36 with considering the absorption correction factor over the 600-630 nm region (Bonacin et al., 2009 and Adarsh et al., 2010) by referring to methylene blue (MB) ($\Phi_{\Delta,MB}$=0.57 in dichloromethane; Li et al., 2013). Therefore, the data suggest the photoactivation of SNile Red is mediated by singlet oxygen, produced by dye sensitization upon irradiation with red light (615/30 nm).

TABLE 1

Photophysical data of thio-caged and uncaged fluorophores.

| Dye[a] | $\lambda_{abs}$(nm) | $\epsilon^{b}$(*10$^4$M$^{-1}$cm$^{-1}$) | $\lambda_{em}$(nm) | ø[c] | Turn-on (x-fold) |
|---|---|---|---|---|---|
| Cou | 261, 378 | 0.95, 2.82 | 445 | 0.71 | — |
| SCou | 273, 476 | 1.43, 2.79 | 453 | <0.001 | 600[d] |
| ACD | 361, 379, 398 | 0.50, 1.0, 1.16 | 406, 428, 455 | 0.64 | — |
| SACD | 430, 456, 485 | 0.52, 1.50, 2.55 | 409, 427, 463 | <0.001 | 180[d] |
| DMAP | 267, 325, 397 | 0.96, 0.52, 0.36 | 505 | 0.09 | — |
| SDMAP | 326, 390, 563 | 3.02, 2.78, 1.02 | 447 | <0.001 | 1600[d] |
| Nile Red | 315, 556 | 0.92, 4.17 | 626 | 0.46 | — |
| SNile Red | 298, 368, 652 | 1.73, 0.97, 4.47 | 616 | <0.001 | 280[e] |
| OPI | 259, 291 | 0.20, 0.19 | 347 | 0.001 | — |
| 1SPI | 298, 332 | 1.20, 1.05 | 328 | <0.001 | 20[d] |
| 2SPI | 262, 387 | 0.61, 2.12 | 294 | <0.001 | 30[d] |

[a]Compounds were dissolved in DMSO (50 μM).
[b]ε: extinction coefficients.
[c]Quantum yields were measured using rhodamine B in ethanol or quinine sulfate in 0.5 M H$_2$SO$_4$ as the reference.
[d]615 nm, 0.4 μW cm$^{-2}$.
[e]470 nm, 0.4 μW cm$^{-2}$.

2. A New Class of Visible Light-Activated Dyes.

Encouraged by the excellent photoactivation properties of SNile Red, Lawesson's reagent was employed to introduce thiocarbonyl moieties into several different fluorophores, such as phthalimide (PI), coumarin (Cou) and acridone (ACD), obtaining yields ranging from 20-80% (FIG. 1). Next, characterization of the spectroscopic and photochemical properties of these thiocaged fluorophores and their oxidized products using UV-vis and fluorescence spectroscopies was performed (Table 1). In general, the UV-vis absorption spectra of the thiocarbonyl fluorophores all exhibited distinct red-shifts compared to their carbonyl analogues. As shown in Table 1, thiocarbonyl group substitution led to significant bathochromic shifts in absorption maxima compared to the corresponding carbonyl compounds. Double thiocarbonyl substitution on 4-dimethylaminophthalimide (4-DMAP, FIG. 1) produced an even larger bathochromic shift of 166 nm. All the thiocarbonyl fluorophores exhibited larger extinction coefficients at their maximal absorption wavelengths than those seen with the corresponding carbonyl compounds. It was hypothesized that the red-shift and enhanced absorption seen with thiocarbonyl compounds were due to the reduced energy gap between the HOMO-LUMO in these fluorophores. This is consistent with the computational results discussed below. More importantly, thiocarbonyl substitutions in all tested fluorophores led to significant reductions in quantum yield, suggesting that replacement of a single oxygen atom with sulfur could be a general strategy for preparing quenched fluorophores with diverse structures. To assess the efficiency of photoactivation for the various thio-caged fluorophores, UV-vis and fluorescence spectra were recorded after different irradiation times (FIGS. 4-8). All the thio-caged fluorophores underwent significant fluorescence enhancement after irradiation with light of appropriate wavelengths (Table 1). In general, the activation efficiencies of thio-caged fluorophores were found to decrease with increasing emission wavelengths.

3. Theoretical Study of Thio-Caged Fluorophores.

Figure 9:
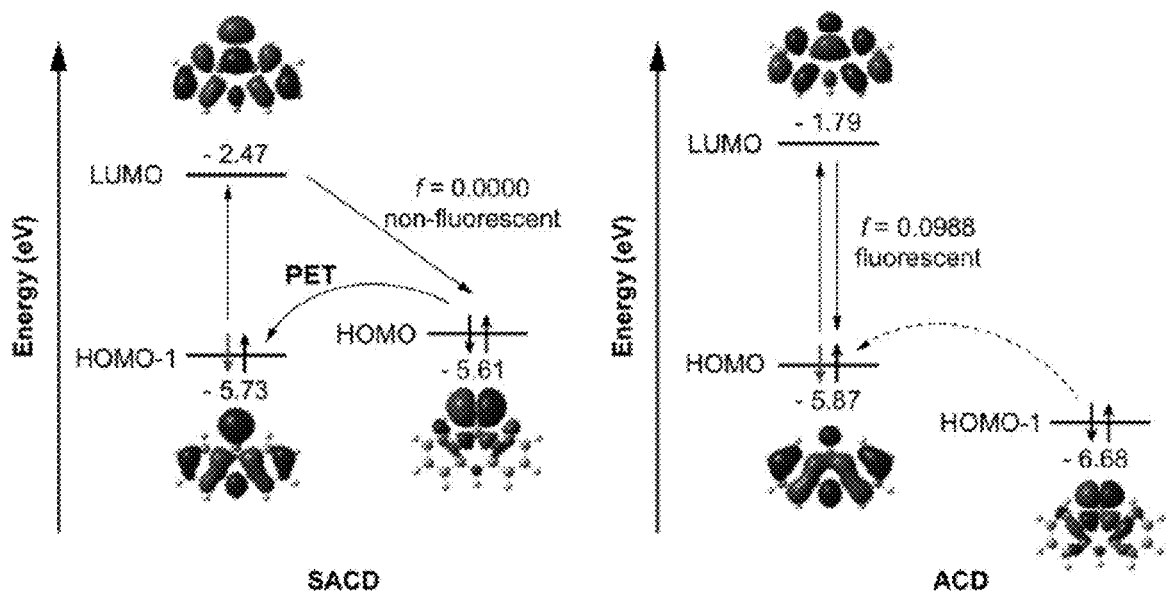
FIG. 9 shows frontier molecular orbital energy levels and electron density of HOMO-1/HOMO/LUMO of SACD (left) and ACD (right). For SACD, the fluorescence is quenched by intramolecular PET from the electron donating thioketone moiety to the first excited single state; photooxidation of the thiocarbonyl moiety to its oxo form lowers the energy of the HOMO-1, which prevents PET and allows for the generation of fluorescence.

To evaluate the mechanism responsible for fluorescence quenching in thiocarbonyl substituted fluorophores, density functional theory (DFT) calculations were performed at a B3LYP/6-31G(d) level to identify the energy levels of frontier molecular orbitals in thio-caged and uncaged fluorophores. Because of the availability of single crystals, acridone (ACD) was used as a model. As shown in FIG. 9, ACD and thio-caged ACD (SACD, FIG. 1) have similar LUMO distributions that are mainly localized on the phenyl ring, whereas the HOMOs of ACD and SACD are distributed on the phenyl ring and sulfur atom, respectively. Regarding the values of LUMO and HOMO levels, SACD has a narrower calculated HOMO-LUMO band gap than ACD, consistent with the observed UV-Vis spectra. Another important parameter provided by time-dependent DFT (TD-DFT) methods is the oscillator strength (f), a dimensionless property that describes the probability of absorption or emission of light upon transferring an electron between two orbitals. The S0→S1 transition for SACD is composed of HOMO/LUMO, and the oscillator strength is 0.0000, suggesting that this transition is forbidden and that the molecule will exhibit no fluorescence. In contrast, the oscillator strength of a low-lying transition-dipole-allowed S0→S1 transition in ACD, composed of HOMO/LUMO, is 0.0988, indicating that the S1 state is emissive and that ACD is fluorescent. Overall, the computational results suggest that single sulfur atom substitutions in fluorophores are able to quench fluorescence via a PET mechanism.

4. Fluorescence Imaging Using Thio-Caged Fluorophores

Figure 10:
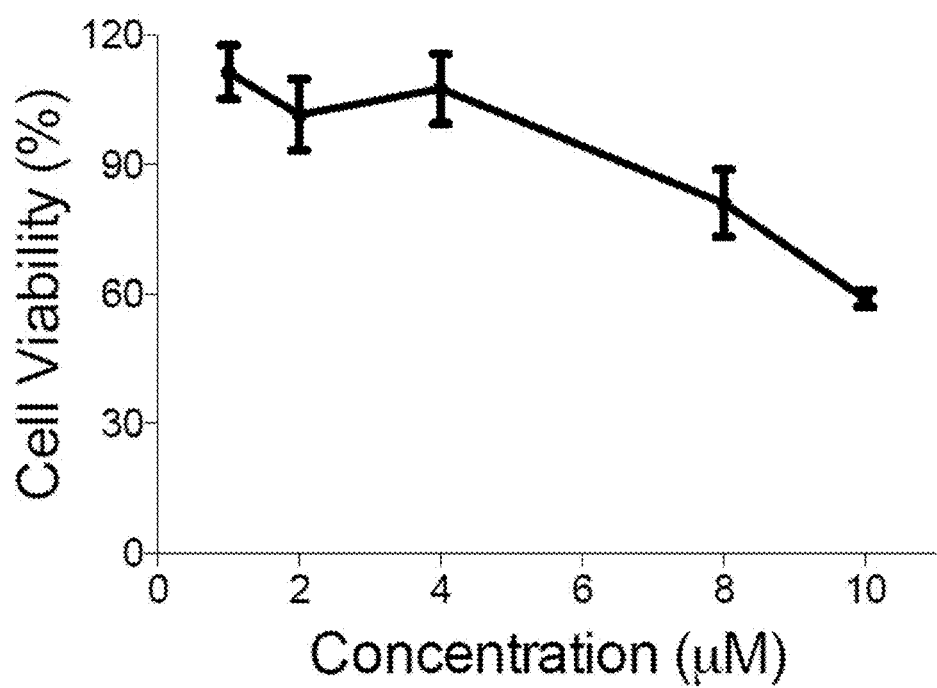
FIG. 10 shows cell viability of SNile Red to 3T3-L1 cells
Figures 11A, 11B, 11C:
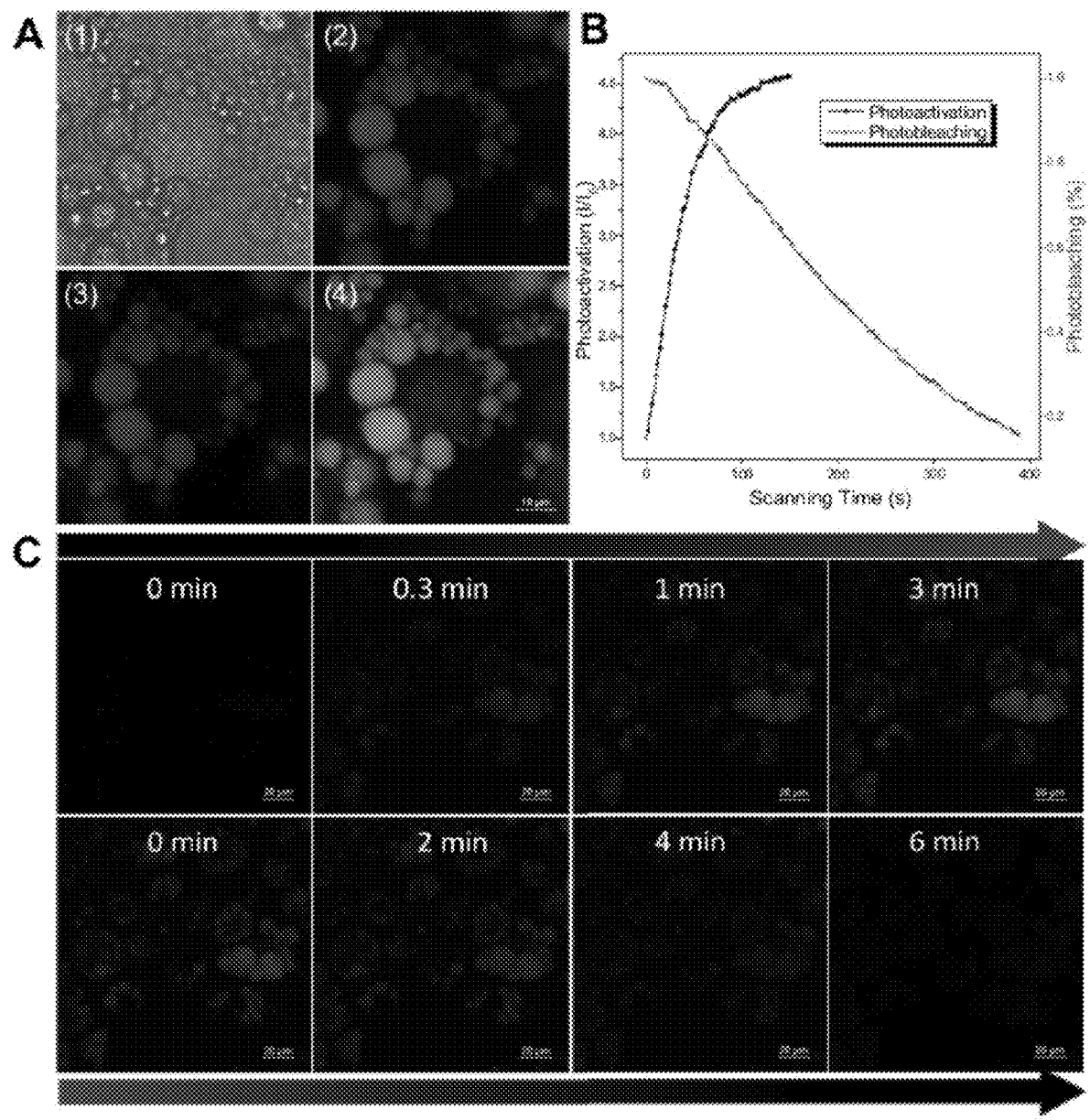
FIGS. 11A-C show (FIG. 11A) signals from photoactivated SNile Red colocalize with the dye BODIPY 493/503. Adipocytes were incubated with SNile Red, BODIPY 493/503, and Hoechst 33342, followed by photoactivation using the 488 nm laser. Scale bar: 10 µm.
Figures 12A, 12B, 12C, 12D, 12E, 12F:
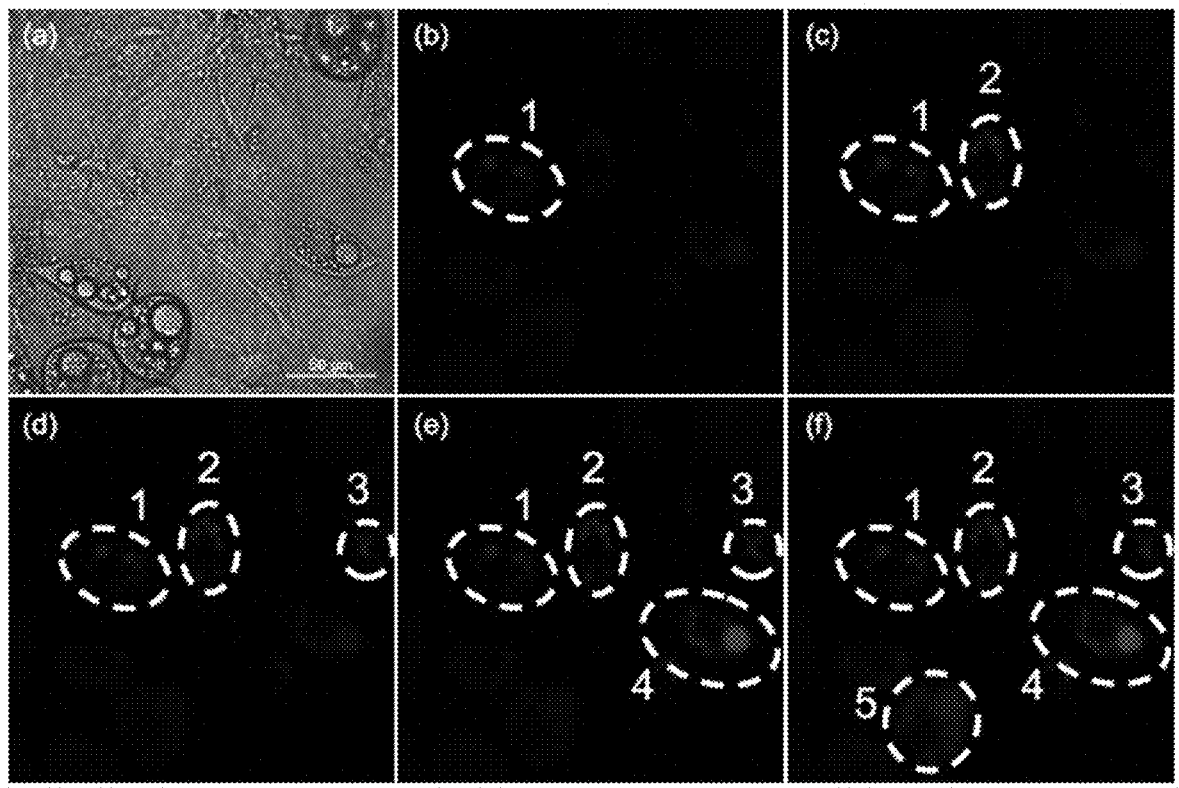
FIGS. 12A-F show bright field of adipocytes (FIG. 12A).

Before testing the utility of thio-caged fluorophores for investigating biological systems, the cytotoxicity of SNile Red in adipocytes was evaluated using Cell Counting Kit-8. At a concentration of 4 μM SNile Red, 90% of 3T3-L1 cells remained viable even after 24 hours (FIG. 10). Thio-caged dyes were then used to obtain subcellular structural data via fluorescence imaging of adipocytes. Nile Red and BODIPY are the fluorescent dyes most commonly used for lipid imaging (Corsaro and Pistara, 1998, Spiller et al., 1998, Tang et al., 2013). Confocal laser scanning microscopy (CLSM) was used to determine the specificity of SNile Red localization in adipocytes differentiated from 3T3-L1 cells. For colocalization studies, adipocytes were stained with 2 μM SNile Red and 100 nM BODIPY 493/503 for 10 mins. BODIPY 493/503 is a lipid droplet-specific fluorophore that exhibits no fluorescence crosstalk with photoactivated SNile Red in confocal imaging. As shown in FIG. 11A, after irradiation with a 488-nm laser for 30 s, adipocytes displayed a globular red fluorescence from photoactivated SNile Red. The SNile Red fluorescence exhibited more than 90% colocalization with BODIPY 493/503 labeling, indicating that the two dyes were localized to the same cellular compartments. The data therefore demonstrate that photoactivated SNile Red preserves the labeling selectivity of Nile Red and can serve as a lipid-droplet specific dye. To demonstrate the feasibility of spatial photo-activation of SNile Red, the 488-nm laser was used to irradiate several groups of adipocytes incubated with SNile Red in a sequential fashion, followed by fluorescence imaging. As shown in FIG. 12, five groups of adipocytes lit up sequentially in the multicellular environment, indicating that the SNile Red photoactivatable probe holds the potential to track with excellent spatial resolution the dynamic events of lipid droplet behavior in a complex biological sample.

5. Super-Resolution Imaging Using Thio-Caged Fluorophores

Figures 13A, 13B, 13C, 13D:
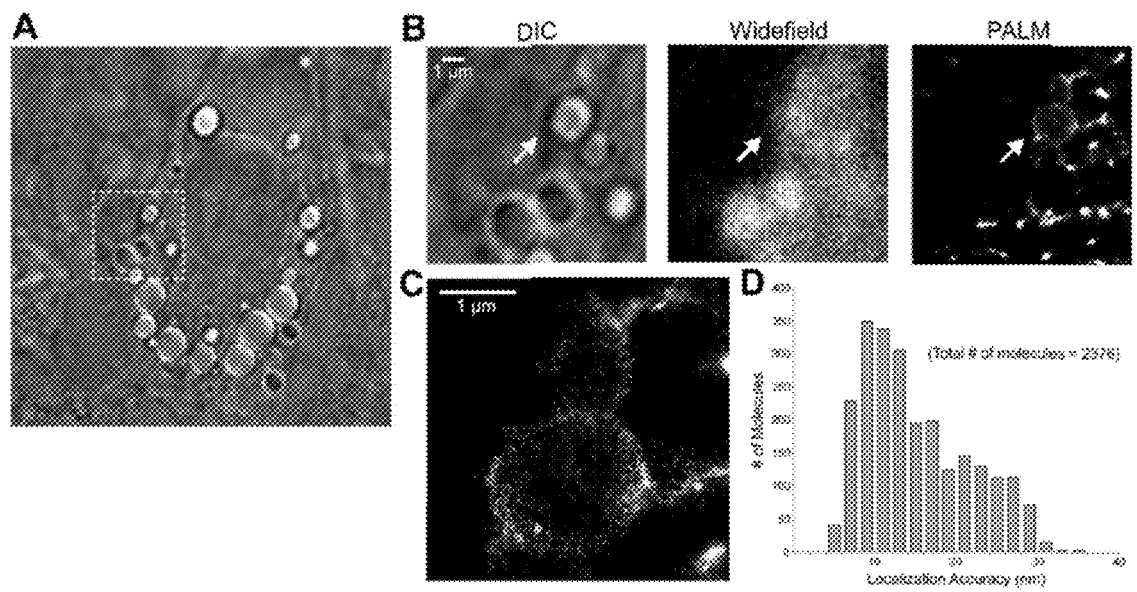
FIGS. 13A-D show (FIG. 13A) differential interference contrast (DIC) image of an adipocyte cell incubated with SNile Red.

Super-resolution imaging based on sequential imaging of a specific region of labeled tissue or cell culture relies on the ability to modulate the fluorescence of fluorophores between dark and bright states (Bates et al., 2007, Sengupta et al., 2014). As described above, SNile Red exhibits an excellent activation ratio of 280-fold, an attractive property for super-resolution imaging. Furthermore, the photoactivation of SNile Red can be achieved using visible light, affording lower phototoxicity and better tissue penetration than use of UV light. To demonstrate the potential of thio-caged fluorophores for super-resolution imaging, CLSM was first used to investigate the processes of photoactivation and photobleaching for SNile Red in living adipocytes. A 488 nm laser was utilized to activate SNile Red, while a 561 nm laser was used for photobleaching. As shown in FIGS. 11B & 11C, differentiated 3T3-L1 adipocytes exhibited no significant fluorescence prior to photoactivation. Following irradiation with the 488-nm laser for 80 s, a five-fold increase of fluorescence intensity was detected. Subsequently, photobleaching was performed in the same cells using the 561-nm laser. As shown in FIGS. 13B & 13D, the fluorescence intensity decayed to 10% of its maximum within 360 s continuous scanning. This photoswitching flexibility holds promise for SNile Red utilization in further photoactivatable localization microscopy (PALM) studies. Next, the utility of SNile Red for performing super-resolution imaging of lipid droplets was explored. Adipocytes differentiated from 3T3-L1 cells were stained with 2 µM SNile Red and then washed prior to PALM imaging. During PALM imaging, SNile Red molecules went through photoactivation and photobleaching processes using high-intensity, simultaneous 405 nm and 561 nm laser stimulation. By capturing bright but sparse, stochastic events for a period of 20,000-30,000 imaging frames, the apparent surface of SNile Red labeled lipid droplets was reconstructed with high molecular accuracy. Compared to the conventional widefield fluorescence image (FIG. 13B) and Differential interference contrast (DIC) image (FIGS. 13A-B), the PALM reconstruction outlines a pair of lipid droplets with a resolution beyond the optical diffraction limit (FIGS. 13B &13C). The precision of localization, judged by error fitting of single molecules using the Thompson equation (Thompson et al., 2002), was roughly 10-20 nm (FIG. 13D). This work, for the first time, has applied a photoactivatable probe to carry out the super-resolution imaging of lipid-droplets in adipocytes.

6. Conclusion

The present disclosure provides a general strategy for preparing photoactivatable probes by performing one or more sulfur-for-oxygen substitutions within fluorescent molecules. Using this strategy, a set of thio-caged fluorophores spanning a broad spectral range was synthesized and characterized. It was found that these thio-caged fluorophores exhibited almost no fluorescence but could be readily converted to their strongly fluorescent oxidized analogues upon irradiation with visible light in air. Calculations indicate that thiocarbonyl substitution in different fluorophores results in significant loss of the fluorescence signal via a photoinduced electron transfer PETquenching mechanism. More importantly, these thio-caged fluorophores can be photoactivated using light with similar wavelengths as their absorbance maxima, rather than UV light with high phototoxicity and low tissue penetration ability. For example, thio-caged Nile Red (SNile Red, $\lambda_{Max}$=652 nm) can be activated by 615 nm red light; thio-caged ACD (SACD, $\lambda_{Max}$=485 nm) can be photo-activated using 470 nm blue light. The utility of thio-caged fluorophores for biological imaging was demonstrated by obtaining unprecedented super-resolution images of lipid droplets with a localization precision of ca. 13 nm. Compared to widely used o-nitrobenzyl photoactivatable dyes, the presently disclosed thio-caged fluorophores have several significant advantages, including ease of design and synthesis, requirement for minimal molecular modification, high efficiency of unmasking using visible light, and superior optical properties. Given the versatility of this strategy for designing photoactivatable dyes, it is envisioned that these thio-caged fluorophores can be used extensively as diverse molecular probes for exploring a wide range of biological processes.

Example 2: Synthesis, Characterization, DFT Calculations, and Imaging Studies Using Thio-Caged Photoactivatable Fluorophores 1. General Experimental Information All solvents and chemicals for synthesis were purchased from Alfa Aesar and Chem-Impex and used as received without further purification, unless otherwise specified. Cellular imaging trackers from Thermo Fisher Scientific.

The $^1$H NMR spectroscopic measurements were carried out using a Bruker-600 NMR at 600 MHz with tetramethysilane (TMS) as internal reference. Electrospray ionization (ESI) mass spectra were performed on a Bruker MicroToF ESI LC-MS System in positive-ion mode. The steady-state absorption spectra were obtained with a ThermoFisher Evolution 220 UV-Vis spectrophotometer in 1 cm path length quartz cells. Fluorescence spectra were recorded using spectrophotometer (SPEX FluoroLog-3). Quantum yield in DMSO was measured relative to the fluorescence of Rhodamine B ($\Phi$=0.65) in ethanol or quinine sulfate ($\Phi$=0.55) in 0.5 M·L$^{-1}$ H$_2$SO$_4$. FT-IR spectrum was taken on a PerkinElmer Spectrum 100 FT-IR Spectrometers. Confocal fluorescent images of living cells were performed using Nikon A1R-si Laser Scanning Confocal Microscope (Japan), equipped with lasers of 405/488/561/638 nm. STORM images were performed on a NSTORM (Nikon, Japan), featuring a CFI Apo TIRF 100× oil objective (NA 1.49) on an inverted Nikon Ti Eclipse microscope with a quad cube filter (Chroma, zt405/488/561/640 m-TRF), piezo stage, and Perfect Focus System (Nikon) for Z-stability. Light source are hand-held UV lamp, BlueView Transilluminator (470 nm centred, Vernier), Prior Lumen200 with 615/30 filter and 850 LED (Mouser Electronics).

2. Synthesis and characterization

General Preparation of Thiocarbonyl Compounds.

To a mixture of carbonyl compounds (0.04 M·L$^{-1}$) and Lawesson's reagent (0.024 M·L$^{-1}$) in a Schlenk flask, 5 mL dry toluene was added. The mixture was heated 120° C. for 1 h and then cooled to room temperature. For the double-thionation compounds (2SPI and SDMAP), mixture of carbonyl compounds (0.04 M·L$^{-1}$) and Lawesson's reagent (0.048 M·L$^{-1}$) was refluxed for 24 h. Solvent was evaporated under reduced pressure. The residue was purified by flash silica gel column chromatography to afford the desired compound as solids in yields of 20-80%.

Figure 14:
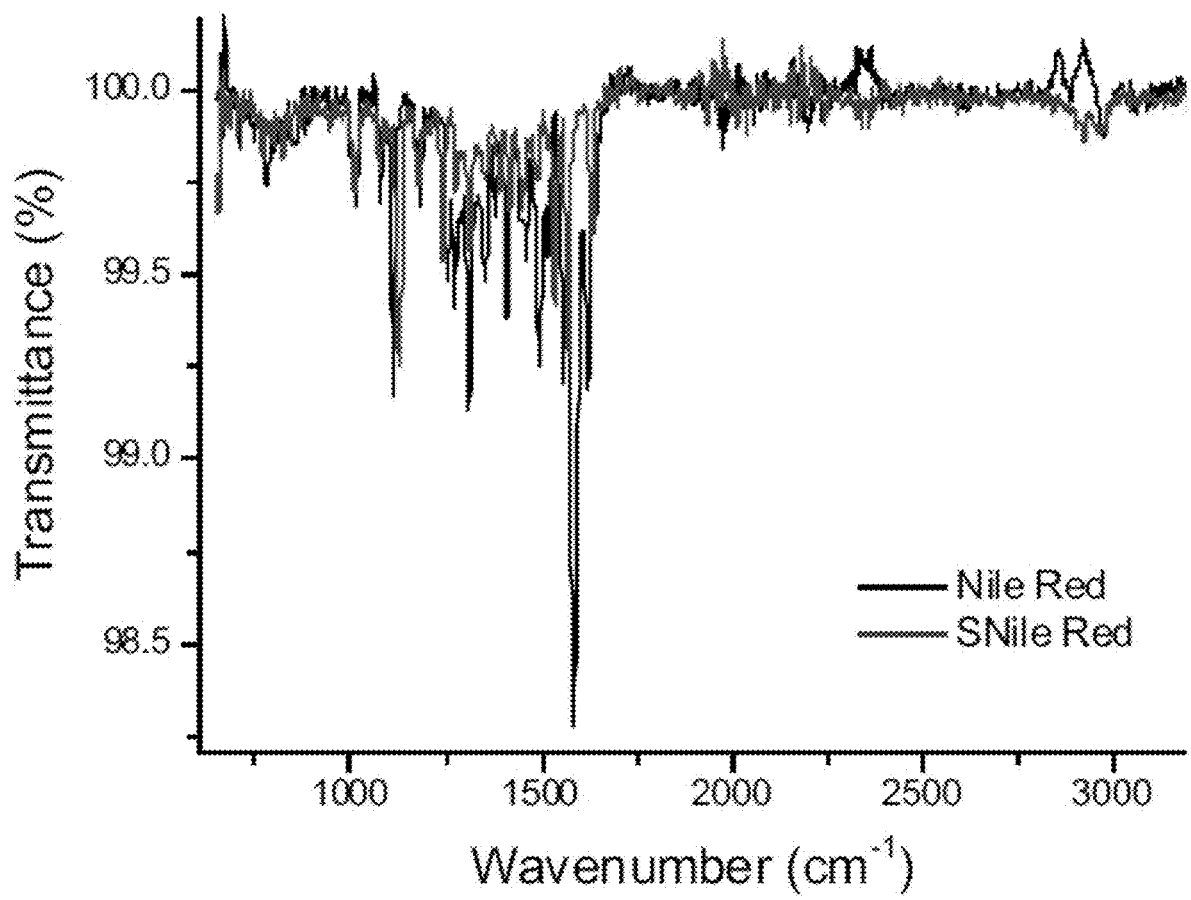
FIG. 14 shows IR spectrum of Nile Red and SNile Red.

SNile Red (40% yield; TLC: ethyl acetate:hexane=1:6, v/v, Rf=0.4). $^1$H NMR (600 MHz, DMSO-d$_6$) δ 8.54 (dd, J=13.7, 8.1 Hz, 2H), 7.76 (t, J=7.5 Hz, 1H), 7.67-7.58 (m, 2H), 6.95 (dd, J=9.2, 2.6 Hz, 1H), 6.70 (t, J=2.2 Hz, 1H), 3.47 (q, J=7.1 Hz, 4H), 1.10 (t, J=7.0 Hz, 6H). $^{13}$C NMR (151 MHz, DMSO-d$_6$) δ 201.59, 152.07, 146.70, 145.38, 139.21, 133.83, 131.41, 130.73, 129.37, 128.35, 127.70, 122.93, 118.30, 112.51, 95.94, 44.88, 12.53. HRMS (ESI): calcd. for C$_{16}$H$_{12}$N$_2$O$_3$ [M+H]$^+$ 281.0921, found 281.0917. IR spectrum shown in FIG. 14.

Figure 15:
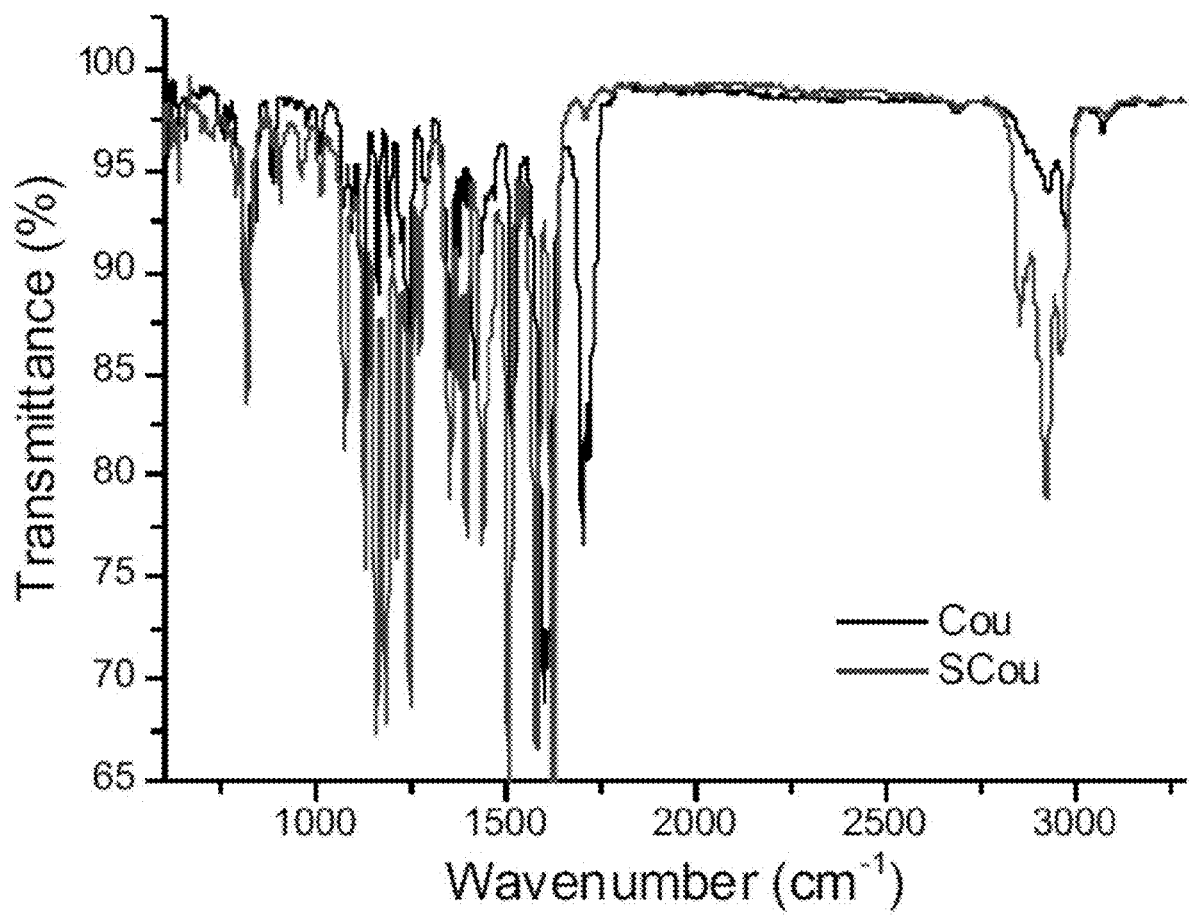
FIG. 15 shows IR spectrum of Cou and SCou.

SCou (80% yield; TLC: ethyl acetate:hexane=1:4, v/v, Rf=0.5), yellow solid. $^1$H NMR (600 MHz, Chloroform-d) δ 7.31 (d, J=2.8 Hz, 1H), 7.29 (d, J=2.6 Hz, 1H), 6.96 (d, J=9.0 Hz, 1H), 6.66 (d, J=2.5 Hz, 1H), 6.64 (dd, J=8.8, 2.5 Hz, 1H), 3.43 (q, J=7.1 Hz, 4H), 1.22 (t, J=7.1 Hz, 6H). $^{13}$C NMR (151 MHz, CDCl$_3$) δ 197.78, 159.56, 151.22, 136.11, 128.87, 123.26, 110.70, 110.28, 97.15, 45.00, 29.72. HRMS (ESI): calcd. for C$_{13}$H$_{16}$NOS [M+H]$^+$ 234.0953, found 234.0874. IR spectrum shown in FIG. 15.

Figure 16:
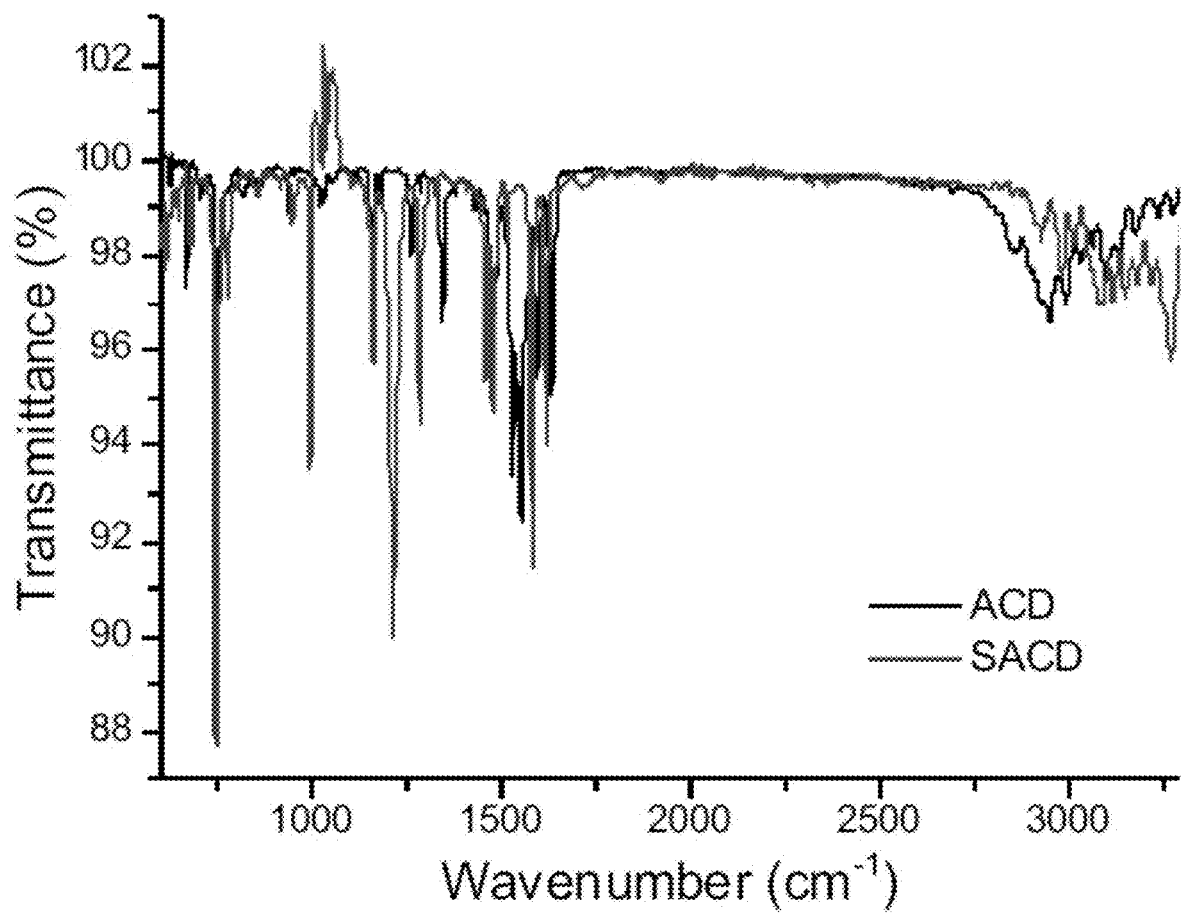
FIG. 16 shows IR spectrum of ACD and SACD.

SACD (80% yield; TLC: ethyl acetate:hexane=1:2, v/v, Rf=0.3), orange solid. $^1$H NMR (600 MHz, DMSO-d$_6$) δ 12.71 (s, 1H), 8.88 (dd, J=8.5, 1.5 Hz, 2H), 8.46-7.74 (m, 2H), 7.69 (d, J=8.4 Hz, 2H), 7.39 (ddd, J=8.2, 6.8, 1.2 Hz, 2H). $^{13}$C NMR (151 MHz, DMSO) δ 197.95, 136.44, 134.32, 130.27, 129.59, 123.61, 119.01. HRMS (ESI): calcd. for C$_{13}$H$_{10}$NS [M+H]$^+$ 212.0534, found 212.0458. IR spectrum shown in FIG. 16.

Figure 17:
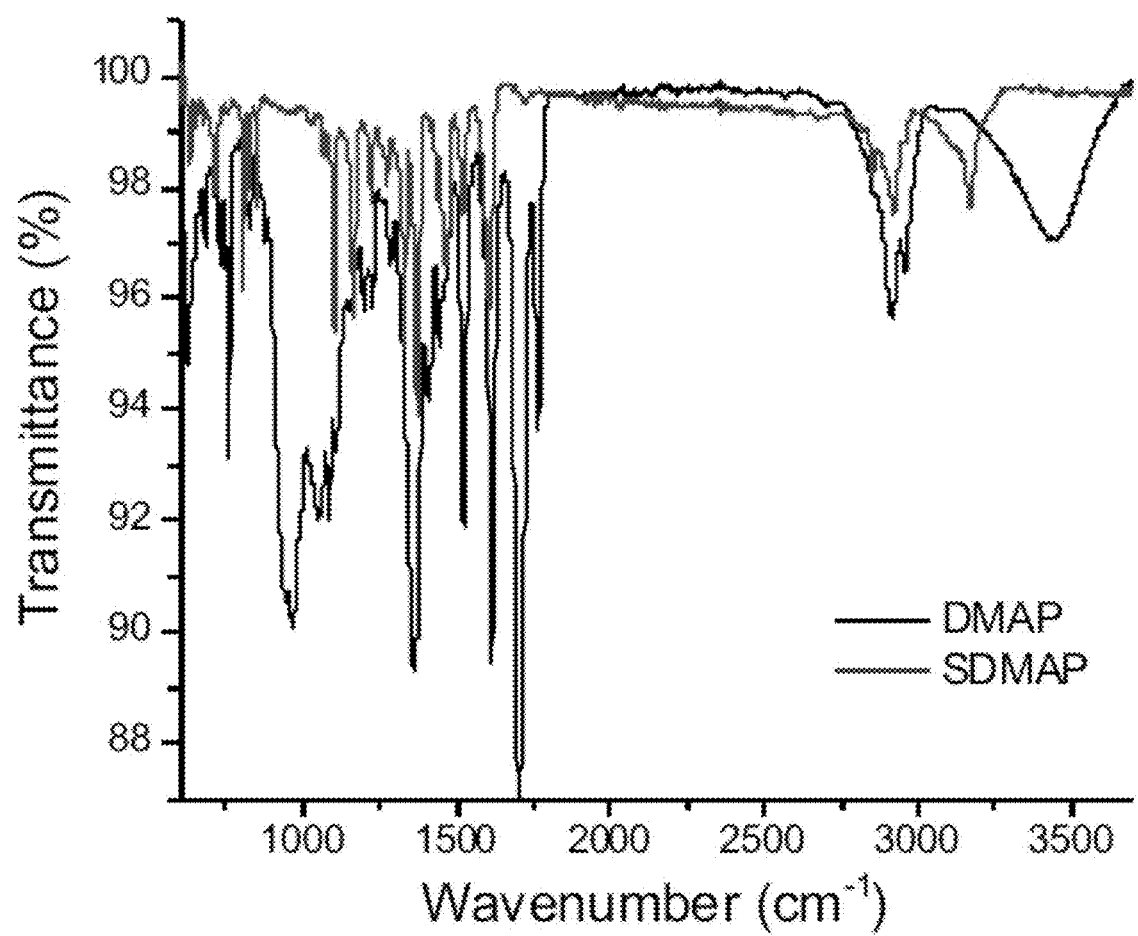
FIG. 17 shows IR spectrum of DMAP and SDMAP.

SDMAP (70% yield; TLC: ethyl acetate:hexane=1:3, v/v, Rf=0.4), purple solid. $^1$H NMR (600 MHz, Chloroform-d) δ 9.36 (s, 1H), 7.70 (d, J=8.6 Hz, 1H), 7.03 (d, J=2.5 Hz, 1H), 6.82 (dd, J=8.7, 2.5 Hz, 1H), 3.17 (s, 6H). $^{13}$C NMR (151 MHz, CDCl$_3$) δ 198.16, 196.01, 154.40, 138.17, 125.39, 123.99, 114.83, 104.78, 40.68. HRMS (ESI): calcd. for C$_{10}$H$_{11}$N$_2$S$_2$ [M+H]$^+$ 223.0364, found 223.0294. IR spectrum shown in FIG. 17

Figure 18:
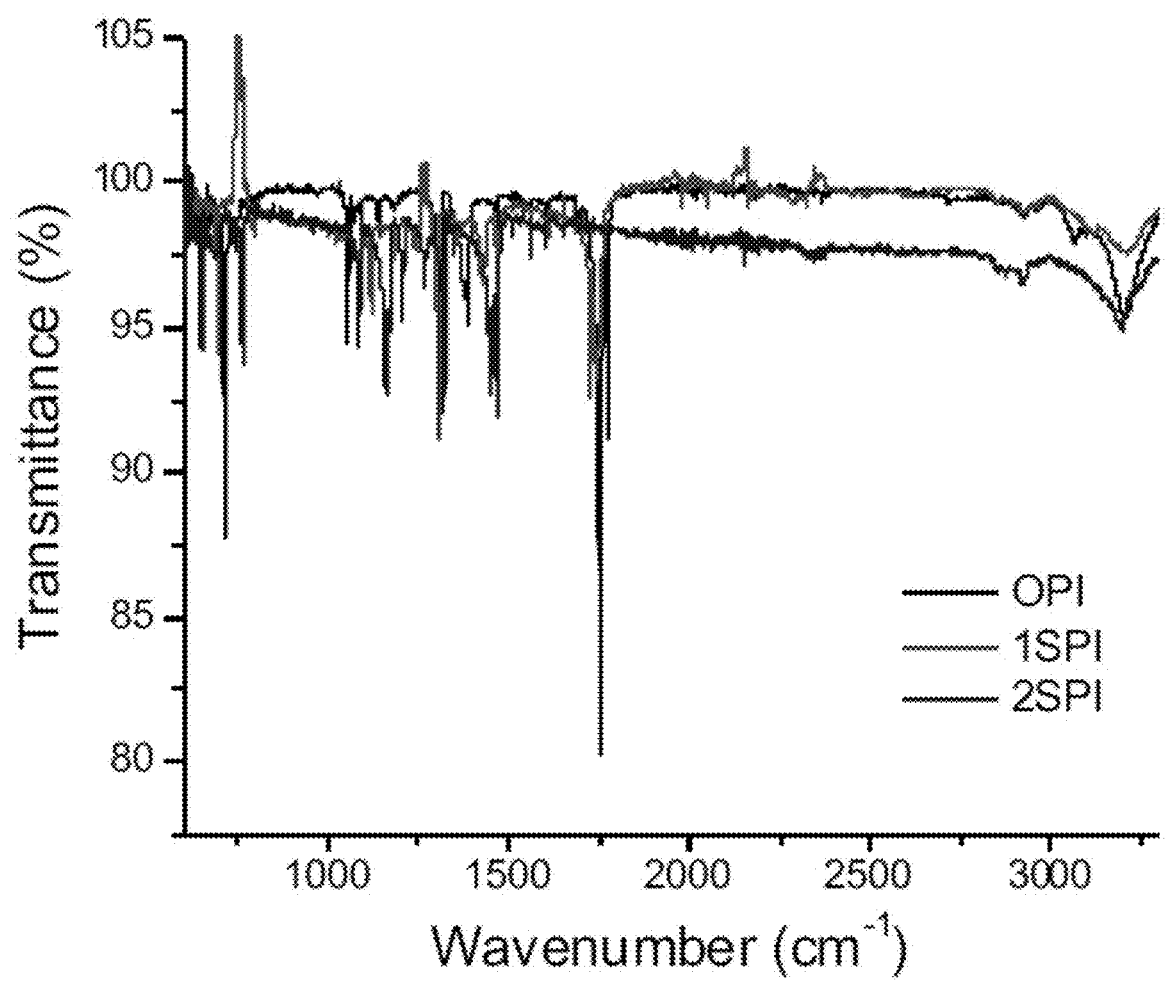
FIG. 18 shows IR spectrum of OPI, 1SPI, and 2SPI.

1SPI (80% yield; TLC: ethyl acetate:hexane=1:2, v/v, Rf=0.5), pink solid. $^1$H NMR (600 MHz, Chloroform-d) δ 8.79 (s, 1H), 7.98 (dd, J=6.4, 1.9 Hz, 1H), 7.83-7.78 (m, 1H), 7.75 (tt, J=7.4, 5.9 Hz, 2H). $^{13}$C NMR (151 MHz, CDCl$_3$) δ 196.88, 169.71, 137.35, 134.36, 133.72, 127.89, 123.98, 123.00. HRMS (ESI): calcd. for C$_8$H$_6$NOS [M+H]$^+$ 164.0170, found 164.0130. IR spectrum shown in FIG. 18.

2SPI (20% yield; TLC: ethyl acetate:hexane=1:2, v/v, Rf=0.7), dark blue solid. $^1$H NMR (600 MHz, Chloroform-d) δ 9.78 (s, 1H), 7.88 (dd, J=5.6, 3.1 Hz, 2H), 7.75 (dd, J=5.6, 3.1 Hz, 2H). $^{13}$C NMR (151 MHz, CDCl$_3$) δ 197.33, 135.08, 133.59, 123.14. HRMS (ESI): calcd. for C$_8$H$_6$NS$_2$ [M+H]$^+$ 179.9942, found 179.9921. IR spectrum shown in FIG. 18.

Figures 19A, 19B:
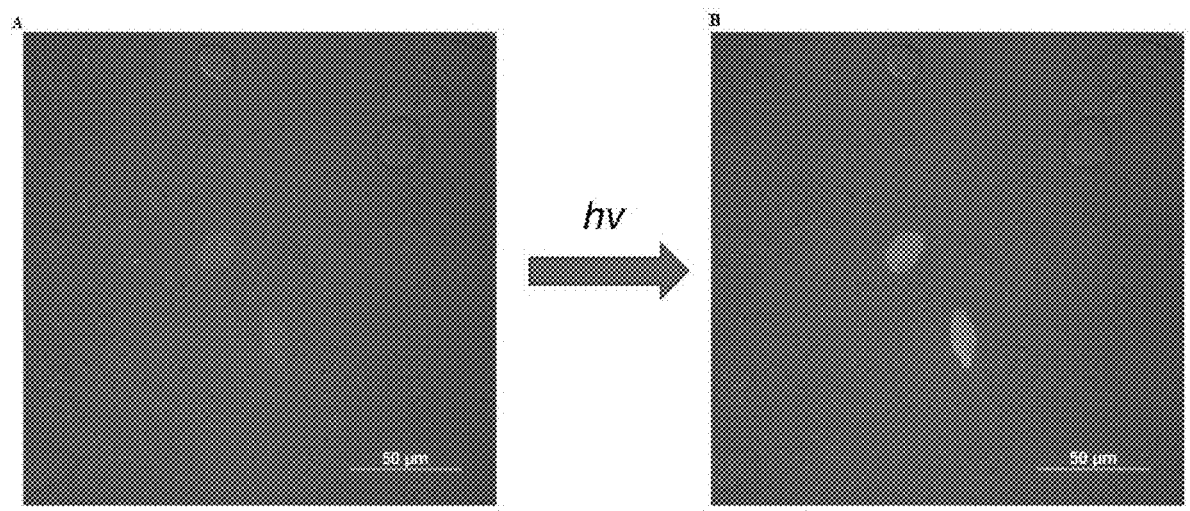
FIGS. 19A & 19B show turn-on of 5NP-Halo in H2B-Halo expressed CHO-K1 cells.

5NP-Halo $^1$H NMR (600 MHz, Chloroform-d) 6 $^1$H NMR (600 MHz, CDCl3) δ 9.04 (d, J=7.9 Hz, 1H), 8.89 (d, J=9.2 Hz, 1H), 8.53 (d, J=8.4 Hz, 1H), 7.46 (t, J=8.1 Hz, 1H), 6.80 (d, J=9.2 Hz, 1H), 6.22 (s, 1H), 5.12 (s, 2H), 3.87-3.80 (m, 4H), 3.59 (dd, J=5.8, 3.8 Hz, 2H), 3.56 (t, J=5.1 Hz, 2H), 3.52 (t, J=6.7 Hz, 2H), 3.50-3.48 (m, 4H), 3.38 (t, J=6.7 Hz, 2H), 2.13 (d, J=6.4 Hz, 4H), 1.76 (dt, J=14.3, 6.8 Hz, 2H), 1.55-1.51 (m, 2H), 1.46-1.39 (m, 2H), 1.37-1.31 (m, 2H). HRMS (ESI): calcd. for C$_{28}$H$_{36}$ClN$_3$NaO$_3$S$_2$$^+$ [M+Na]$^+$ 584.1779, found 584.1777. H$_2$B-Halo expressed CHO-K1 cells were treated with 5NP-Halo (10 μM; see FIGS. 19A & 19B). The synthesis of 5NP-Halo is shown below in Scheme 1.

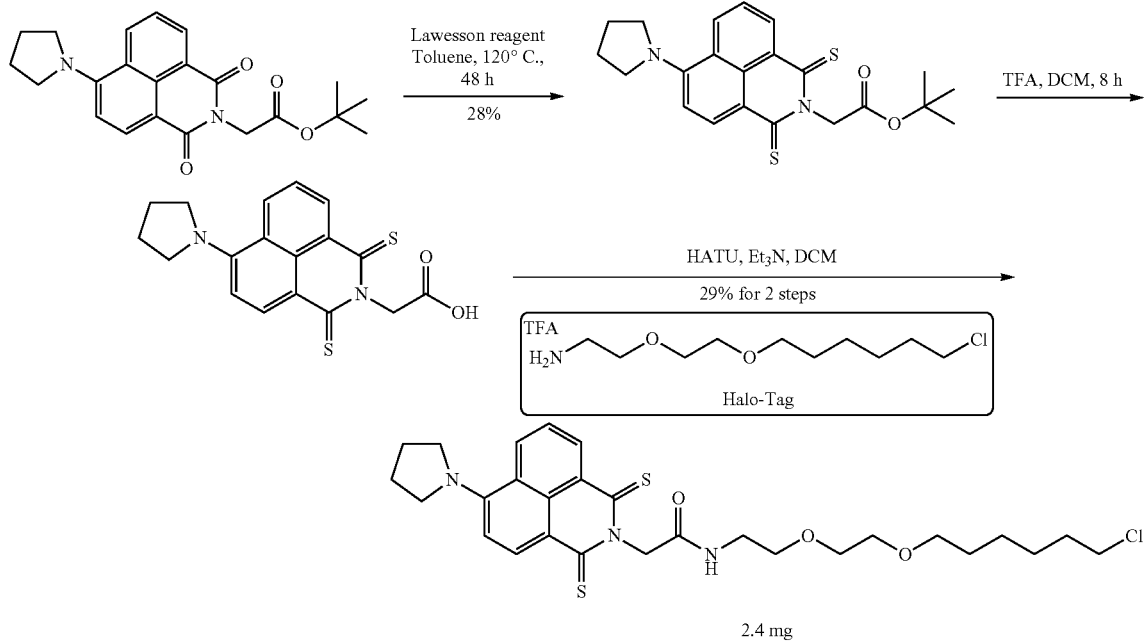

Scheme 1. Outline of synthesis of 5NP-Halo.

3. Quantum Yield Determination

Quantum yields were measured with Rhodamine B as reference (Φ=0.65) or quinine sulfate (Φ=0.55) in 0.5 M H$_2$SO$_4$. Fluorescence measurements were performed in 1 cm quartz cells with 5 μM samples in DMSO on spectrophotometer (SPEX FluoroLog-3) (slits 5×5). The fluorescence quantum yield, Φ (sample), were calculated according to equation as following:

$$\frac{\Phi_{sample}}{\Phi_{ref}} = \frac{OD_{ref} \cdot I_{sample} \cdot d_{sample}^2}{OD_{sample} \cdot I_{ref} \cdot d_{ref}^2}$$

Φ: quantum yield; I: integrated emission intensity; OD: optical density at the excitation wavelength; d: refractive index of solvents, dDMSO=1.478; $d_{ethanol}$=1.36; $d_{water}$=1.33.

4. Singlet Oxygen Quantum Yield Determination

Singlet oxygen quantum yields were calculated according to the literature (Bonacin et al., 2009, Adarsh et al., 2010, and Li et al., 2013). The initial absorbance of DPBF was adjusted to about 1.0 in DCM. The photosensitizer was added to the cuvette and photosensitizer's absorbance was adjusted to under 0.2 to minimize the possibility of singlet oxygen quenching by the dyes. The photooxidation of DPBF was monitored by UV-vis spectra over 100 s. The quantum yield of singlet oxygen generation was calculated by a relative method comparing to the methylene blue (MB) ($\Phi_{\Delta,MB}$=0.57 in DCM) as the reference. $\Phi_\Delta$ were calculated according to the following equation:

$$\Phi_{\Delta,SNR} = \Phi_{\Delta,MB} \cdot \frac{m_{SNR} F_{MB}}{m_{MB} F_{SNR}}$$

The subscript 'SNR' designates SNile Red, m is the slope of the plot ΔA of DPBF (at 410 nm) vs. irradiation time, and F is the absorption correction factor, which is given by:

$$F = \int (1-10^{-OD}) d\lambda$$

OD at the irradiation wavelength (600-630 nm).

5. DFT Calculation

For the theoretical study of photophysical properties of SACD, density functional theory (DFT) and time-dependent density functional theory (TD-DFT) methods were performed and the Becke's three-parameter hybrid exchange functional with Lee-Yang-Parr gradient-corrected correlation (B3LYP functional) was used with 6-31G** for main group elements, as implemented in the Gaussian 09 package. Geometries for sulfonium ZnSalens were fully optimized without symmetry constraints. The solvent effect was involved through the PCM approach (DMSO, ε=46.826). The vibration frequency calculations at the same level were carried out to confirm each stationary point to be either a minimum. The vertical excitation energies were then calculated based on the optimized geometries of the SACD molecules.

6. Cell Culture

3T3-L1 cells were incubated in complete medium (Dulbecco's modified Eagle's Medium (DMEM), supplemented with 10% fetal bovine serum (FBS) and 1% penicillin-streptomycin) at 37° C. in atmosphere containing 5% $CO_2$. Differentiation medium is a mixture of 90% DMEM, 10% Fetal Bovine Serum (FBS), 1.0 µM Dexamethasone, 0.5 mM Methylisobutylxanthine (IBMX) and 1.0 µg·mL Insulin. Adipocyte maintenance medium is a mixture of 90% DMEM 10% Fetal Bovine Serum and 1.0 µg·mL Insulin.

7. CCK-8 Assay

3T3-L1 cells were seeded in flat-bottomed 96-well plates, 1×10⁴ cells per well, with 200 µL complete culture media for 24 h. After washed with PBS for three times, the cells were incubated with different concentrations of SNile Red. All stock solutions were prepared in DMSO (0.5 mM) and diluted with complete medium. After cultured for 24 h, the cells were washed with PBS (pH 7.4) three times. 10 µL Cell Counting Kit-8 (CCK-8) solution and 90 µl PBS (pH 7.4) were added per well simultaneously. After 2 hours, the absorbance at 450 nm was read by 96-well plates reader. The viability of Hela cells was calculated by the following equation:

$$CV = (As-Ab)/(Ac-Ab) \times 100\%$$

CV stands for the viability of cells, As, Ac and Ab stand for the absorbance of cells containing SNile Red cell control (0 µM SNile Red) and blank control (wells containing neither cells nor SNile Red).

8. Co-Localization Assay

3T3-L1 cells were differentiated to adipocytes according to the protocol from ATCC (Chemically-induced differentiation of at CC® CL-173TM (3T3-L1) using single-Component Commercially-available reagents). 3T3-L1 cells were placed onto 0.1 mM poly-D-lysine coated glasses in complete media and were induced to differentiate. A stock solution of SNile Red in chromatographic grade, anhydrous DMSO was prepared as 2 mM. The solution was diluted to a final concentration of 2 µM by complete growth medium. Stock solution of Bodipy 493/503 were prepared as 1 mM, and the stock solution was diluted to the working concentration in complete medium (100 nM).

After incubation of 2 µM SNile Red for 10 min, cells were washed with PBS (pH 7.4) twice and turned to confocal laser scanning microscope (CLSM). Images were taken under conditions as follows: 60× immersion lens with a resolution of 1024×1024 and a speed of 0.5 frame per second, 561 nm excitation wavelength and 552 to 617 nm detector slit, 20% laser power for dye, and 488 nm excitation wavelength and 500 to 530 nm detector slit, 5% laser power for Bodipy 493/503. Differential interference contrast (DIC) and fluorescent images were processed and analyzed using ImageJ. The Pearson's Coefficient was calculated by ImageJ.

9. PALM Image Acquisition and Analysis

3T3-L1 adipocytes were plated on glass bottom dishes (MatTek 35 mm dish, No. 1.5 coverslip) and differentiated. Just prior to PALM imaging, cells were washed and incubated with 2 uM SNile Red in DMEM complete media for 10 minutes at room temperature in the dark before washing and subsequent imaging in 1×PBS (pH 7.4).

Imaging was performed at room temperature on the Nikon N-STORM system, featuring a CFI Apo TIRF 100× oil objective (NA 1.49) on an inverted Nikon Ti Eclipse microscope with a quadcube filter (Chroma, zt405/488/561/640 m-TRF), piezo stage, and Perfect Focus System (Nikon) for Z-stability. Lasers used in this study: 50 mW 405 nm diode laser and 200 mW 561 nm solidstate lasers within an agilent MLC400B laser combiner with AOTF modulation.

PALM imaging was controlled with NIS-Elements Ar software and captured by an Andor iXON DU 897 EMCCD camera (EM gain setting=100, pixel size=160 nm, 512×512 pixel field) with a cylindrical lens inserted in the light path (for greater molecule counts during analysis, see below). Fluorescent lipid droplets were identified, and the laser incident angle was adjusted to near TIRF for an optimal signal-noise ratio. Maximum 405/561 nm laser power (simultaneous) was used to photobleach SNile Red fluorescence and acquisition frames were collected upon observing spontaneous reactivation fluorescent events within lipid droplets. Imaging frames were collected for a total of 20,000-30,000 frames. Using an independent power meter, maximum laser power was measured directly above the objective as 4 mW for 405 nm and 34.8 mW for 561 nm.

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the disclosure. All variations and modifications apparent to those skilled in the art are deemed to be within the spirit, scope, and concept of the disclosure as defined by the appended claims.

IX. REFERENCES

The following references to the extent that they provide exemplary procedural or other details supplementary to those set forth herein, are specifically incorporated herein by reference.

Anderson, *Practical Process Research & Development—A Guide for Organic Chemists*, 2$^{nd}$ ed., Academic Press, New York, 2012.
*Handbook of Pharmaceutical Salts: Properties, and Use*, Stahl and Wermuth Eds., Verlag Helvetica Chimica Acta, 2002.
Reagan-Shaw et al., *FASEB J.*, 22(3):659-661, 2008.
Smith, *March's Advanced Organic Chemistry: Reactions, Mechanisms, and Structure*, 7$^{th}$ Ed., Wiley, 2013.
Adarsh et al., *Org. Lett.*, 12(24):5720-5723, 2010.
Atilgan et al., *Angewandte Chemie International Edition*, 53(40):10678-10681, 2014.
Bates et al., *Science*, 317(5845):1749-1753, 2007.
Benelli et al., In: *Molecular Switches*; Wiley-Blackwell; pp 697-717, 2011.
Bonacin et al., *Journal of the Brazilian Chemical Society*, 20(1):31-36, 2009.
Brieke et al., *Angewandte Chemie International Edition*, 51(34):8446-8476, 2012.
Brown et al., *Biophys J*, 76(1 Pt 1):489-499, 1999.
Ceroni and Balzani, In: *The Exploration of Supramolecular Systems and Nanostructures by Photochemical Techniques*; Ceroni, P., Ed.; Lecture Notes in Chemistry; Springer Netherlands: Dordrecht; pp 21-38, 2012.
Choi et al., *Chem. Commun.*, 24:3560-3562, 2009.
Chozinski et al., *FEBS Letters*, 588(19):3603-3612, 2014.
Corsaro and Pistara, *Tetrahedron*, 54(50):15027-15062, 1998.
Coyle, *Tetrahedron*, 41(23):5393-5425, 1985.
Dexter, *J. Chem. Phys.*, 21(5):836-850, 1953.
Fam et al., *Materials*, 11(9):1768, 2018.
Firster, *Discuss. Faraday Soc.*, 27(O):7-17, 1959.
Goldberg et al., *J. Am. Chem. Soc.*, 132(42):14718-14720, 2010.
Goldberg et al., *J. Am. Chem. Soc.*, 134(14):6088-6091, 2012.
Goldberg et al., *J. Am. Chem. Soc.*, 135(49):18651-18658, 2013.
Goswami et al., *Journal of the American Chemical Society*, 137(11):3783-3786, 2015.
Gould et al., *J. Am. Chem. Soc.*, 116(18):8188-8199, 1994.
Grimm et al., In: Progress in *Molecular Biology and Translational Science*; Morris, M. C., Ed.; Fluorescence—Based Biosensors; Academic Press, 113:1-34, 2013.
Grimm et al., *Nat. Methods*, 13(12):985-988, 2016.
Huang et al., *Chem. Commun.*, 52(50):7798-7801, 2016.
Lavis et al., *ACS Chem. Biol.*, 1(4):252-260, 2006.
Lee et al., *ACS Chemical Biology*, 4(6):409-427, 2009.
Li and Zheng, *Photochemical & Photobiological Sciences*, 11(3):460, 2012.
Li et al., *RSC Adv.*, 3(32):13417-13421, 2013.
Moon et al., *Tetrahedron Letters*, 53(48):6594-6597, 2012.
Nani et al., *Angewandte Chemie*, 127(46): 13839-13842, 2015.
Park et al., *Inorg Chem*, 51(5):2880-2884, 2012.
Peterson et al., *Journal of the American Chemical Society*, 140(23):7343-7346, 2018.
Puliti et al., *Bioorganic & Medicinal Chemistry*, 19(3):1023-1029, 2011.
Puliti et al., *Bioorganic & Medicinal Chemistry*, 19(3):1023-1029, 2011.
Rubinstein et al., *Chem. Commun.*, 51(29):6369-6372, 2015.
Sengupta et al., *Chem. Rev.*, 114(6):3189-3202, 2014.
Spiller et al., *Journal of Porphyrins and Phthalocyanines*, 2(2):145-158, 1998.
Tang et al., *Chem. Sci.*, 5(2):558-566, 2013.
Thompson et al., *Biophys J*, 82(5):2775-2783, 2002.
Tran et al., *Organic Letters*, 17(3):402-405, 2015.
Ueno et al., *Journal of the American Chemical Society*, 126(43):14079-14085, 2004.

What is claimed is:
1. A photoactivatable fluorophore defined as:

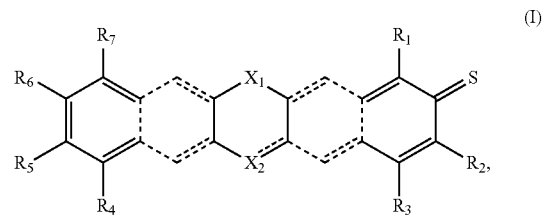

(I)

wherein:
X$_1$ is —O—, —S—, —C(O)—, —C(S)—, —NR$_a$—, or —Si(R$_u$)(R$_{u'}$)—, wherein:
R$_a$ is hydrogen, alkyl$_{(C\leq8)}$, substituted alkyl$_{(C\leq8)}$, acyl$_{(C\leq8)}$, or substituted acyl$_{(C\leq8)}$;
R$_u$ and R$_{u'}$ are each independently alkyl$_{(C\leq8)}$, substituted alkyl$_{(C\leq8)}$, aryl$_{(C\leq12)}$, or substituted aryl$_{(C\leq12)}$;
X$_2$ is —N=, —C(R$_b$)=, or —C(R$_c$)(R$_d$)— wherein:
R$_b$ is hydrogen; or
alkyl$_{(C\leq8)}$, substituted alkyl$_{(C\leq8)}$, aryl$_{(C\leq12)}$, or substituted aryl$_{(C\leq12)}$;
R$_c$ and R$_d$ are taken together to form a group of the formula:

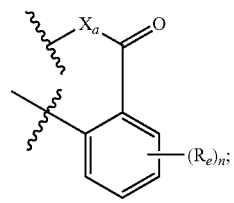

wherein:
n is 0, 1, 2, 3, or 4;
R$_e$ at each instance is independently hydrogen, halo, hydroxy, or amino; or alkyl$_{(C≤8)}$, alkoxy$_{(C≤8)}$, alkylamino$_{(C≤8)}$, dialkylamino$_{(C≤8)}$, or a substituted version of any of these groups; or $X_a$ is —O— or —NR$_f$—, wherein:
  R$_f$ is hydrogen; or
    alkyl$_{(C≤8)}$, substituted alkyl$_{(C≤8)}$, acyl$_{(C≤8)}$, or substituted acyl$_{(C≤8)}$; or
  -C(S)NHR$_g$, wherein:
    R$_g$ is alkyl$_{(C≤8)}$, substituted alkyl$_{(C≤8)}$, alkenyl$_{(C≤8)}$, or substituted alkenyl$_{(C≤8)}$;

R$_1$ is hydrogen, halo, hydroxy, amino, nitro, or cyano; or
  alkyl$_{(C≤8)}$, alkoxy$_{(C≤8)}$, alkylamino$_{(C≤8)}$, dialkylamino$_{(C≤8)}$, amido$_{(C≤8)}$, or a substituted version of any of these groups; or
—C(O)R$_h$, wherein;
  R$_h$ is hydroxy or amino; or
    alkyl$_{(C≤8)}$, alkoxy$_{(C≤8)}$, alkylamino$_{(C≤8)}$, dialkylamino$_{(C≤8)}$, or a substituted version of any of these groups; and R$_2$, R$_3$, R$_4$, R$_5$, R$_6$, and R$_7$ are each independently hydrogen, halo, hydroxy, amino, nitro, or cyano; or
  alkyl$_{(C≤8)}$, alkoxy$_{(C≤8)}$, alkylamino$_{(C≤8)}$, dialkylamino$_{(C≤8)}$, amido$_{(C≤8)}$, or a substituted version of any of these groups; or
—C(O)R$_i$, wherein;
  R$_i$ is hydroxy or amino; or
    alkyl$_{(C≤8)}$, alkoxy$_{(C≤8)}$, alkylamino$_{(C≤8)}$, dialkylamino$_{(C≤8)}$, or a substituted version of any of these groups; or R$_2$ and R$_3$, R$_4$ and R$_5$, R$_5$ and R$_6$, or R$_6$ and R$_7$ are taken together to form an arene$_{(C≤12)}$, a substituted arene$_{(C≤12)}$, a heteroarene$_{(C≤12)}$, or a substituted heteroarene$_{(C≤12)}$; or a photoactivatable fluorophore of the formula:

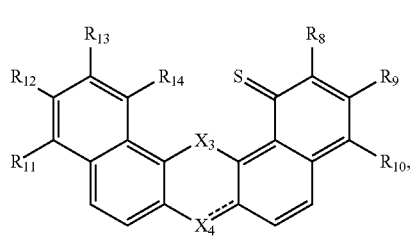

(II)

wherein:
  $X_3$ is —O—, —S—, —C(O)—, —C(S)—, —NR$_j$—, or —Si(R$_v$)(R$_{v'}$)—, wherein:
    R$_j$ is hydrogen, alkyl$_{(C≤8)}$, substituted alkyl$_{(C≤8)}$, acyl$_{(C≤8)}$, or substituted acyl$_{(C≤8)}$;
    R$_v$ and R$_{v'}$ are each independently alkyl$_{(C≤8)}$, substituted alkyl$_{(C≤8)}$, aryl$_{(C≤12)}$, or substituted aryl$_{(C≤12)}$;
  $X_4$ is —N=, —C(R$_k$)=, or —C(R$_l$)(R$_m$)— wherein:
    R$_k$ is hydrogen; or
      alkyl$_{(C≤8)}$, substituted alkyl$_{(C≤8)}$, aryl$_{(C≤12)}$, or substituted aryl$_{(C≤12)}$;

R$_l$ and R$_m$ are taken together to form a group of the formula:

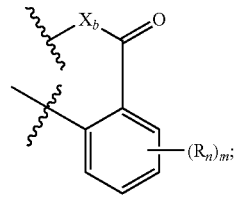

wherein:
  m is 0, 1, 2, 3, or 4;
  R$_n$ at each instance is independently hydrogen, halo, hydroxy, or amino; or
    alkyl$_{(C≤8)}$, alkoxy$_{(C≤8)}$, alkylamino$_{(C≤8)}$, dialkylamino$_{(C≤8)}$, or a substituted version of any of these groups; or
  $X_b$ is —O— or —NR$_o$—, wherein:
    R$_o$ is hydrogen; or
      alkyl$_{(C≤8)}$, substituted alkyl$_{(C≤8)}$, acyl$_{(C≤8)}$, or substituted acyl$_{(C≤8)}$; or
    -C(S)NHR$_p$, wherein:
      R$_p$ is alkyl$_{(C≤8)}$, substituted alkyl$_{(C≤8)}$, alkenyl$_{(C≤8)}$, or substituted alkenyl$_{(C≤8)}$;

R$_8$, R$_9$, R$_{10}$, R$_{11}$, R$_{12}$, R$_{13}$, and R$_{14}$ are each independently hydrogen, halo, hydroxy, amino, nitro, or cyano; or
  alkyl$_{(C≤8)}$, alkoxy$_{(C≤8)}$, alkylamino$_{(C≤8)}$, dialkylamino$_{(C≤8)}$, amido$_{(C≤8)}$, or a substituted version of any of these groups; or
—C(O)R$_q$, wherein;
  R$_q$ is hydroxy or amino; or
    alkyl$_{(C≤8)}$, alkoxy$_{(C≤8)}$, alkylamino$_{(C≤8)}$, dialkylamino$_{(C≤8)}$, or a substituted version of any of these groups; or R$_8$ and R$_9$, R$_9$ and R$_{10}$, R$_{11}$ and R$_{12}$, R$_{12}$ and R$_{13}$, or R$_{13}$ and R$_{14}$ are taken together to form an arene$_{(C≤12)}$, a substituted arene$_{(C≤12)}$, a heteroarene$_{(C≤12)}$, or a substituted heteroarene$_{(C≤12)}$; or a photoactivatable fluorophore of the formula:

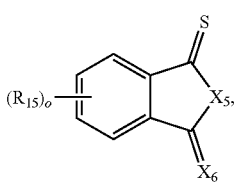

(III)

wherein:
  o is 0, 1, 2, 3, or 4;
  $X_5$ is —O— or —NR$_r$—, wherein:
    R$_r$ is hydrogen; or
      alkyl$_{(C≤8)}$, substituted alkyl$_{(C≤8)}$, acyl$_{(C≤8)}$, or substituted acyl$_{(C≤8)}$; or
    —C(O)R$_s$, wherein:
      R$_s$ is hydroxy or amino; or
        alkyl$_{(C≤8)}$, alkoxy$_{(C≤8)}$, alkylamino$_{(C≤8)}$, dialkylamino$_{(C≤8)}$, or a substituted version of any of these groups;
  $X_6$ is =O or =S; and
  R$_{15}$ at each instance is independently hydrogen, halo, hydroxy, amino, nitro, or cyano; or alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
—C(O)R$_t$, wherein;
R$_t$ is hydroxy or amino; or
alkyl$_{(C\leq 8)}$, alkoxy$_{(C\leq 8)}$, alkylamino$_{(C\leq 8)}$, dialkylamino$_{(C\leq 8)}$, or a substituted version of any of these groups; or or a pharmaceutically acceptable salt or tautomer of any of these formulae.

2. The photoactivatable fluorophore of claim 1, wherein the photoactivatable fluorophore is further defined as:

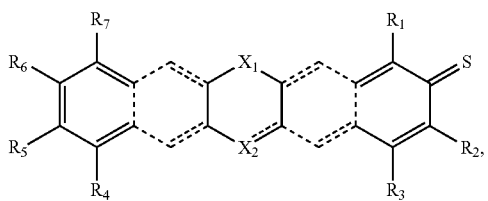

(I)

wherein:
X$_1$ is —O—, —S—, —C(O)—, —C(S)—, or —NR$_a$—, wherein:
R$_a$ is hydrogen, alkyl$_{(C\leq 8)}$, substituted alkyl$_{(C\leq 8)}$, acyl$_{(C\leq 8)}$, or substituted acyl$_{(C\leq 8)}$;
X$_2$ is —N=, —C(R$_b$)=, or —C(R$_c$)(R$_d$)— wherein:
R$_b$ is hydrogen; or
alkyl$_{(C\leq 8)}$, substituted alkyl$_{(C\leq 8)}$, aryl$_{(C\leq 12)}$, or substituted aryl$_{(C\leq 12)}$;
R$_c$ and R$_d$ are taken together to form a group of the formula:

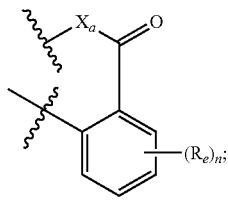

wherein:
n is 0, 1, 2, 3, or 4;
R$_e$ at each instance is independently hydrogen, halo, hydroxy, or amino; or
alkyl$_{(C\leq 8)}$, alkoxy$_{(C\leq 8)}$, alkylamino$_{(C\leq 8)}$, dialkylamino$_{(C\leq 8)}$, or a substituted version of any of these groups; or
X$_a$ is —O— or —NR$_f$—, wherein:
R$_f$ is hydrogen; or
alkyl$_{(C\leq 8)}$, substituted alkyl$_{(C\leq 8)}$, acyl$_{(C\leq 8)}$, or substituted acyl$_{(C\leq 8)}$; or
-C(S)NHR$_g$, wherein:
R$_g$ is alkyl$_{(C\leq 8)}$, substituted alkyl$_{(C\leq 8)}$, alkenyl$_{(C\leq 8)}$, or substituted alkenyl$_{(C\leq 8)}$;
R$_1$ is hydrogen, halo, hydroxy, amino, nitro, or cyano; or
alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
—C(O)R$_h$, wherein;
R$_h$ is hydroxy or amino; or alkyl$_{(C\leq 8)}$, alkoxy$_{(C\leq 8)}$, alkylamino$_{(C\leq 8)}$, dialkylamino$_{(C\leq 8)}$, or a substituted version of any of these groups; and
R$_2$, R$_3$, R$_4$, R$_5$, R$_6$, and R$_7$ are each independently hydrogen, halo, hydroxy, amino, nitro, or cyano; or
alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
—C(O)R$_i$, wherein;
R$_i$ is hydroxy or amino; or
alkyl$_{(C\leq 8)}$, alkoxy$_{(C\leq 8)}$, alkylamino$_{(C\leq 8)}$, dialkylamino$_{(C\leq 8)}$, or a substituted version of any of these groups; or
R$_2$ and R$_3$, R$_4$ and R$_5$, R$_5$ and R$_6$, or R$_6$ and R$_7$ are taken together to form an arene$_{(C\leq 12)}$, a substituted arene$_{(C\leq 12)}$, a heteroarene$_{(C\leq 12)}$, or a substituted heteroarene$_{(C\leq 12)}$;

or a pharmaceutically acceptable salt or tautomer thereof.

3. The photoactivatable fluorophore of claim 1, wherein the photoactivatable fluorophore is further defined as:

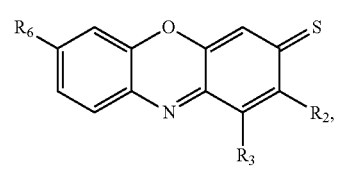

(VII)

wherein:
R$_2$ and R$_3$ are taken together to form an arene$_{(C\leq 12)}$, a substituted arene$_{(C\leq 12)}$, a heteroarene$_{(C\leq 12)}$, or a substituted heteroarene$_{(C\leq 12)}$; and
R$_6$ is hydrogen, halo, hydroxy, amino, nitro, or cyano; or
alkyl$_{(C\leq 8)}$, alkoxy$_{(C\leq 8)}$, alkylamino$_{(C\leq 8)}$, dialkylamino$_{(C\leq 8)}$, amido$_{(C\leq 8)}$, or a substituted version of any of these groups; or
—C(O)R$_i$, wherein;
R$_i$ is hydroxy or amino; or
alkyl$_{(C\leq 8)}$, alkoxy$_{(C\leq 8)}$, alkylamino$_{(C\leq 8)}$, dialkylamino$_{(C\leq 8)}$, or a substituted version of any of these groups;

or a pharmaceutically acceptable salt or tautomer thereof.

4. The photoactivatable fluorophore of claim 1, wherein R$_2$ and R$_3$ are taken together to form an arene$_{(C\leq 12)}$ or a substituted arene$_{(C\leq 12)}$.

5. The photoactivatable fluorophore of claim 1, wherein R$_6$ is hydroxy, amino, alkylamino$_{(C\leq 8)}$, substituted alkylamino$_{(C\leq 8)}$, dialkylamino$_{(C\leq 8)}$, substituted dialkylamino$_{(C\leq 8)}$, amido$_{(C\leq 8)}$, or substituted amido$_{(C\leq 8)}$.

6. The photoactivatable fluorophore of claim 1, wherein the photoactivatable fluorophore is further defined as:

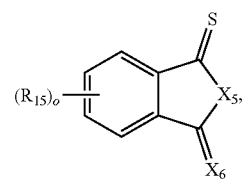

(III)

wherein:
o is 0, 1, 2, 3, or 4;
$X_5$ is —O— or —NR$_r$—, wherein:
$R_r$ is hydrogen; or
alkyl$_{(C≤8)}$, substituted alkyl$_{(C≤8)}$, acyl$_{(C≤8)}$, or substituted acyl$_{(C≤8)}$; or
—C(O)R$_s$, wherein:
$R_s$ is hydroxy or amino; or
alkyl$_{(C≤8)}$, alkoxy$_{(C≤8)}$, alkylamino$_{(C≤8)}$, dialkylamino$_{(C≤8)}$, or a substituted version of any of these groups;
$X_6$ is =O or =S; and
$R_{15}$ at each instance is independently hydrogen, halo, hydroxy, amino, nitro, or cyano; or
alkyl$_{(C≤8)}$, alkoxy$_{(C≤8)}$, alkylamino$_{(C≤8)}$, dialkylamino$_{(C≤8)}$, amido$_{(C≤8)}$, or a substituted version of any of these groups; or
—C(O)R$_t$, wherein;
$R_t$ is hydroxy or amino; or
alkyl$_{(C≤8)}$, alkoxy$_{(C≤8)}$, alkylamino$_{(C≤8)}$, dialkylamino$_{(C≤8)}$, or a substituted version of any of these groups;
or a pharmaceutically acceptable salt or tautomer thereof.

7. A photoactivatable fluorophore is further defined as:

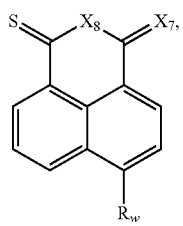

(XI)

wherein:
$X_7$ is O or S;
$X_8$ is —O— or —NR$_x$—, wherein
$R_x$ is hydrogen or substituted alkyl$_{(C≤8)}$; or
—S$_1$-L$_1$-S$_2$—R$_y$, wherein:
S$_1$ is a covalent bond, -alkanediyl$_{(C≤8)}$—, or substituted -alkanediyl$_{(C≤8)}$—;
L$_1$ is a covalent bond or —C(O)—, —C(O)O—, or —C(O)NR$_z$—, wherein:
R$_z$ is hydrogen, alkyl$_{(C≤8)}$, or substituted alkyl$_{(C≤8)}$; and
S$_2$ is a covalent bond or —(CH$_2$CH$_2$O)$_n$—, wherein n is from 0 to 10;
R$_y$ is alkyl$_{(C≤8)}$ or substituted alkyl$_{(C≤8)}$; and
R$_w$ is heterocycloalkyl$_{(C≤8)}$ or substituted heterocycloalkyl$_{(C≤8)}$;
or a pharmaceutically acceptable salt or tautomer thereof.

8. The photoactivatable fluorophore of claim 1, wherein S$_1$ is -alkanediyl$_{(C≤8)}$.

9. The photoactivatable fluorophore of claim 8, wherein S$_1$ is —CH$_2$—.

10. The photoactivatable fluorophore of claim 1, wherein R$_z$ is hydrogen.

11. The photoactivatable fluorophore of claim 1, wherein n is 2.

12. The photoactivatable fluorophore of claim 1, wherein R$_y$ is substituted alkyl$_{(C≤8)}$.

13. The photoactivatable fluorophore of claim 1, wherein R$_y$ is 1-chlorohex-6-yl.

14. The photoactivatable fluorophore of claim 1, wherein the photoactivatable fluorophore is further defined as:

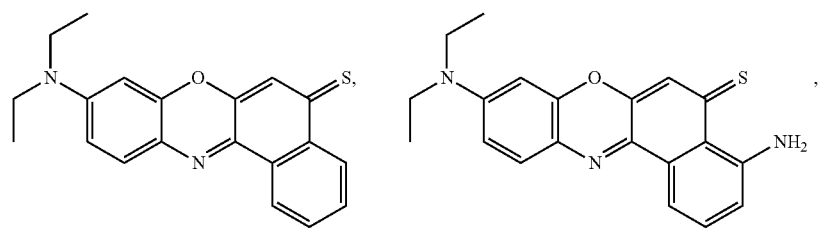

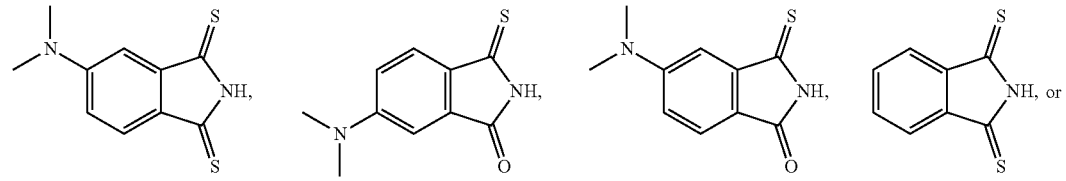

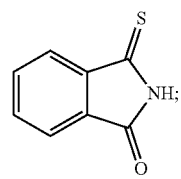

or a pharmaceutically acceptable salt or tautomer thereof.

15. A conjugate of the formula:

T-L-E, wherein:
E is a photoactivatable fluorophore of claim 1;
L is a covalent bond or a linker; and
T is a targeting moiety;
or a pharmaceutically acceptable salt thereof.

16. A composition comprising:
(a) a conjugate of claim 15; and
(b) an excipient.

* * * * *

UNITED STATES PATENT AND TRADEMARK OFFICE
CERTIFICATE OF CORRECTION

PATENT NO. : 11,913,884 B2
APPLICATION NO. : 16/798992
DATED : February 27, 2024
INVENTOR(S) : Han Xiao and Juan Tang It is certified that error appears in the above-identified patent and that said Letters Patent is hereby corrected as shown below:

In the Claims

In Claim 1, Column 51, Line 9, delete "-C(S)NHR$_g$," and insert -- —C(S)NHR$_g$,-- therefor.

In Claim 1, Column 51, Line 63, delete "—N=" and insert -- —N═-- therefor.

In Claim 1, Column 52, Line 25, delete "-C(S)NHR$_p$," and insert -- —C(S)NHR$_p$,-- therefor.

In Claim 2, Column 53, Line 30, delete "-C(S)NHR$_g$," and insert -- —C(S)NHR$_g$,-- therefor.

In Claim 2, Column 53, Line 59, delete "-C(S)NHR$_g$," and insert -- —C(S)NHR$_g$,-- therefor.

In Claim 7, Column 56, Line 6, delete "—S$_1$–L$_1$–S$_2$—R$_y$" and insert -- —S$_1$—L$_1$—S$_2$—R$_y$—C(S)NHR$_g$,-- therefor.

In Claim 7, Column 56, Line 7, delete "-alkanediyl$_{(C\leq 8)}$—" and insert -- —alkanediyl$_{(C\leq 8)}$— -- therefor.

In Claim 7, Column 56, Line 8, delete "-alkanediyl$_{(C\leq 8)}$—" and insert -- —alkanediyl$_{(C\leq 8)}$— -- therefor.

In Claim 8, Column 56, Line 22, delete "-alkanediyl$_{(C\leq 8)}$—" and insert -- —alkanediyl$_{(C\leq 8)}$— -- therefor.

Signed and Sealed this
Ninth Day of July, 2024

Katherine Kelly Vidal
*Director of the United States Patent and Trademark Office*